(12) United States Patent
Blake, III

(10) Patent No.: US 10,779,838 B1
(45) Date of Patent: Sep. 22, 2020

(54) INSTRUMENT FOR SERIALLY APPLYING CLIPS TO A SURGICAL SITE

(71) Applicant: Joseph W Blake, III, New Canaan, CT (US)

(72) Inventor: Joseph W Blake, III, New Canaan, CT (US)

( * ) Notice: Subject to any disclaimer, the term of this patent is extended or adjusted under 35 U.S.C. 154(b) by 913 days.

(21) Appl. No.: 14/121,344

(22) Filed: Aug. 22, 2014

Related U.S. Application Data

(60) Provisional application No. 61/962,661, filed on Nov. 13, 2013.

(51) Int. Cl.
*A61B 17/128* (2006.01)
*A61B 17/122* (2006.01)

(52) U.S. Cl.
CPC ........ *A61B 17/1285* (2013.01); *A61B 17/122* (2013.01)

(58) Field of Classification Search
CPC ............ A61B 17/0487; A61B 17/0488; A61B 17/068; A61B 17/0682; A61B 17/122; A61B 17/1227; A61B 17/128; A61B 17/1285; A61B 2017/0409; A61B 2017/0488; A61B 2017/049; A61B 17/10
See application file for complete search history.

(56) References Cited

U.S. PATENT DOCUMENTS

| | | | |
|---|---|---|---|
| 600,504 A | 3/1898 | Autio | |
| 1,498,488 A | 6/1924 | Stallings | |
| 2,455,833 A | 12/1948 | Trombetta | |
| 2,490,741 A | 12/1949 | Pashby | |
| 2,744,251 A | 5/1956 | Vollmer | |
| 2,927,171 A | 3/1960 | Rhodes | |
| 2,959,172 A | 11/1960 | Held | |
| 3,047,874 A | 8/1962 | Kelsey | |
| 3,098,232 A | 7/1963 | Brown | |
| 3,120,230 A | 2/1964 | Skold | |
| 3,230,758 A | 1/1966 | Klingler | |
| 3,263,504 A | 8/1966 | Parkinson | |
| 3,545,444 A | 12/1970 | Green | |
| RE27,146 E | 6/1971 | Rozmus | |
| 3,638,847 A | 2/1972 | Noiles et al. | |
| 3,646,801 A | 3/1972 | Caroli | |
| 3,777,538 A | 12/1973 | Weatherly | |
| 3,819,100 A | 6/1974 | Noiles | |
| 3,844,289 A | 10/1974 | Noiles | |

(Continued)

*Primary Examiner* — Eric J Rosen
*Assistant Examiner* — Mikail A Mannan
(74) *Attorney, Agent, or Firm* — Patrick J. Walsh

(57) ABSTRACT

An instrument for applying clips in surgery particularly suited for microsurgery with instrument chassis and cover joined to form housing supporting handle and clip handling components, the handle for squeeze and release action to develop linear reciprocation motion of fixed excursion, the clip handling components for feeding a stack of clips one-by-one into instrument clip crimping jaws for application at a surgical site, an anti-backup mechanism constraining handle action to full pull and release strokes, and an instrument lock-out mechanism to prevent instrument operation after last clip in stack is used. Clip handling components of magazine carrier, magazine, clip stack, clip pusher, pusher spring, and pusher spring shaft are inserted into instrument in upwardly open channel and secured by pusher spring cover.

30 Claims, 33 Drawing Sheets

(56) References Cited

U.S. PATENT DOCUMENTS

| | | | |
|---|---|---|---|
| 3,949,924 | A | 4/1976 | Green |
| 4,166,466 | A | 9/1979 | Jarvik |
| 4,196,836 | A | 4/1980 | Becht |
| 4,204,623 | A | 5/1980 | Green |
| 4,242,902 | A | 1/1981 | Green |
| 4,246,903 | A | 1/1981 | Larkin |
| 4,296,751 | A | 10/1981 | Blake, III et al. |
| 4,367,746 | A | 1/1983 | Derechinsky |
| 4,372,316 | A | 2/1983 | Blake, III et al. |
| 4,408,603 | A * | 10/1983 | Blake, III .......... A61B 17/0682 206/339 |
| 4,425,915 | A | 1/1984 | Ivanov |
| 4,430,997 | A | 2/1984 | DiGiovani et al. |
| 4,448,194 | A | 5/1984 | DiGiovani |
| 4,480,640 | A | 11/1984 | Becht |
| 4,492,232 | A | 1/1985 | Green |
| 4,532,925 | A | 7/1985 | Blake, III |
| 4,562,839 | A | 1/1986 | Blake, III |
| 4,572,183 | A | 2/1986 | Juska |
| 4,616,650 | A | 10/1986 | Green et al. |
| 4,624,254 | A | 11/1986 | McGarry et al. |
| 4,662,374 | A | 5/1987 | Blake, III |
| 4,850,355 | A | 7/1989 | Brooks et al. |
| 5,047,038 | A | 9/1991 | Peters et al. |
| 5,084,057 | A | 1/1992 | Green et al. |
| 5,100,420 | A | 3/1992 | Green et al. |
| 5,104,395 | A * | 4/1992 | Thornton .............. A61B 17/128 606/143 |
| 5,171,247 | A | 12/1992 | Hughett |
| D332,660 | S | 1/1993 | Rawson |
| 5,192,288 | A | 3/1993 | Thompson et al. |
| 5,271,727 | A | 12/1993 | Haber et al. |
| 5,289,963 | A | 3/1994 | McGarry et al. |
| 5,290,302 | A | 3/1994 | Pericic |
| 5,308,357 | A | 5/1994 | Lichtman |
| 5,366,134 | A | 11/1994 | Green et al. |
| 5,370,658 | A | 12/1994 | Scheller et al. |
| D354,564 | S | 1/1995 | Medema |
| 5,403,327 | A | 4/1995 | Thornton et al. |
| 5,431,668 | A | 7/1995 | Burbank, III et al. |
| 5,484,095 | A | 1/1996 | Green et al. |
| 5,527,318 | A | 6/1996 | McCarry |
| 5,527,326 | A | 6/1996 | Herman et al. |
| 5,591,178 | A | 1/1997 | Green et al. |
| 5,607,436 | A | 3/1997 | Pratt et al. |
| 5,623,854 | A | 4/1997 | Snider |
| 5,634,930 | A | 6/1997 | Thornton et al. |
| 5,645,551 | A | 7/1997 | Green et al. |
| 5,681,330 | A | 10/1997 | Hughett et al. |
| 5,700,270 | A | 12/1997 | Peyser et al. |
| 5,700,271 | A | 12/1997 | Whitfield et al. |
| 5,720,756 | A | 2/1998 | Green et al. |
| 5,725,537 | A | 3/1998 | Green et al. |
| 5,725,538 | A | 3/1998 | Green et al. |
| 5,833,696 | A | 11/1998 | Whitfield et al. |
| 5,833,698 | A | 11/1998 | Hinchliffe et al. |
| 5,868,761 | A | 2/1999 | Nicholas et al. |
| 5,893,873 | A | 4/1999 | Rader et al. |
| 5,904,693 | A | 5/1999 | Dicesare et al. |
| 5,938,667 | A | 8/1999 | Peyser |
| 5,951,574 | A | 9/1999 | Stefanchik et al. |
| 5,993,465 | A | 11/1999 | Shipp |
| 6,024,748 | A | 2/2000 | Manzo et al. |
| 6,171,316 | B1 | 1/2001 | Kovac et al. |
| 6,277,131 | B1 | 8/2001 | Kalikow |
| 6,348,054 | B1 | 2/2002 | Allen |
| 6,423,079 | B1 | 7/2002 | Blake, III |
| 6,849,079 | B1 | 2/2005 | Blake, III et al. |
| 6,855,156 | B2 | 2/2005 | Etter et al. |
| 6,869,435 | B2 | 3/2005 | Blake, III |
| 6,911,033 | B2 | 6/2005 | De Guillebon et al. |
| 7,141,056 | B2 | 11/2006 | Manetakis |
| 7,261,724 | B2 | 8/2007 | Molitor |
| 7,264,625 | B1 | 9/2007 | Buncke |
| 7,288,098 | B2 | 10/2007 | Huitema |
| 7,297,149 | B2 | 11/2007 | Vitali |
| 7,585,304 | B2 | 9/2009 | Hughett |
| 7,621,926 | B2 | 11/2009 | Wixey et al. |
| 7,637,917 | B2 | 12/2009 | Whitfield et al. |
| 7,717,926 | B2 | 5/2010 | Whitfield et al. |
| 7,731,724 | B2 | 6/2010 | Huitema |
| 8,075,571 | B2 | 12/2011 | Vitali |
| 8,172,870 | B2 | 5/2012 | Shipp |
| 8,187,287 | B1 | 5/2012 | Blake |
| 8,236,012 | B2 | 8/2012 | Vitali |
| 8,262,679 | B2 | 9/2012 | Nguyen |
| 8,267,944 | B2 | 9/2012 | Sorrentino |
| 8,267,945 | B2 | 9/2012 | Nguyen |
| 8,267,946 | B2 | 9/2012 | Whitfield |
| 8,282,655 | B2 | 10/2012 | Whitfield |
| 8,357,171 | B2 | 1/2013 | Whitfield |
| 8,409,223 | B2 | 4/2013 | Sorrentino |
| 8,480,688 | B2 | 7/2013 | Boulnois |
| 8,496,673 | B2 | 7/2013 | Nguyen |
| 8,523,882 | B2 | 9/2013 | Huitema |
| 8,529,588 | B2 | 9/2013 | Ahlberg |
| 8,545,486 | B2 | 10/2013 | Malkowski |
| 8,747,423 | B2 | 6/2014 | Whitfield et al. |
| 8,753,356 | B2 | 6/2014 | Vitali et al. |
| 8,814,884 | B2 | 8/2014 | Whitfield et al. |
| 8,894,665 | B2 | 11/2014 | Sorrentino et al. |
| 8,915,930 | B2 | 12/2014 | Huitema |
| 8,920,438 | B2 | 12/2014 | Aranyi et al. |
| 8,968,337 | B2 | 3/2015 | Whitfield et al. |
| 9,011,464 | B2 | 4/2015 | Zammataro |
| 9,011,465 | B2 | 4/2015 | Whitfield |
| 9,089,334 | B2 | 7/2015 | Sorrentino |
| 9,113,892 | B2 | 8/2015 | Malkowski |
| 9,113,893 | B2 | 8/2015 | Sorrentino |
| 9,186,153 | B2 | 11/2015 | Zammataro |
| 9,271,737 | B2 | 3/2016 | Castro et al. |
| 9,326,776 | B2 | 5/2016 | Gadberry et al. |
| 9,491,608 | B2 | 11/2016 | Naito et al. |
| 2002/0002374 | A1 | 1/2002 | Barreiro |
| 2002/0049472 | A1 | 4/2002 | Coleman |
| 2002/0128668 | A1 | 9/2002 | Manetakis et al. |
| 2003/0014060 | A1 | 1/2003 | Wilson |
| 2003/0023249 | A1 | 1/2003 | Manetakis |
| 2003/0135224 | A1 | 7/2003 | Blake, III |
| 2008/0140090 | A1* | 6/2008 | Aranyi ............... A61B 17/1285 606/143 |
| 2011/0144665 | A1* | 6/2011 | Malkowski ........ A61B 17/1285 606/143 |
| 2013/0165951 | A1 | 6/2013 | Blake, III |
| 2014/0052157 | A1 | 2/2014 | Whitfield |
| 2014/0379003 | A1 | 12/2014 | Blake, III |
| 2015/0005790 | A1 | 1/2015 | Whitfield et al. |

* cited by examiner

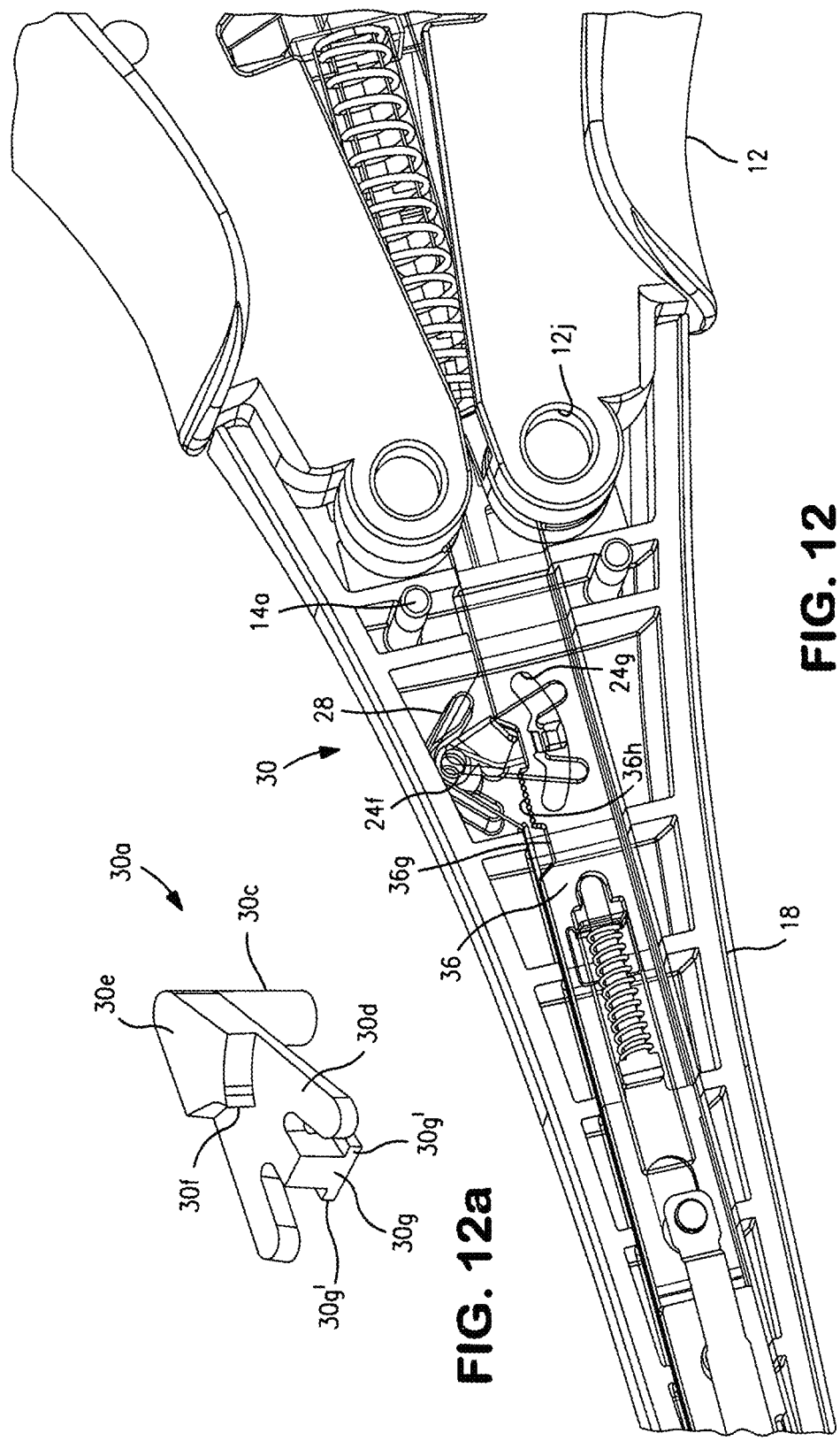

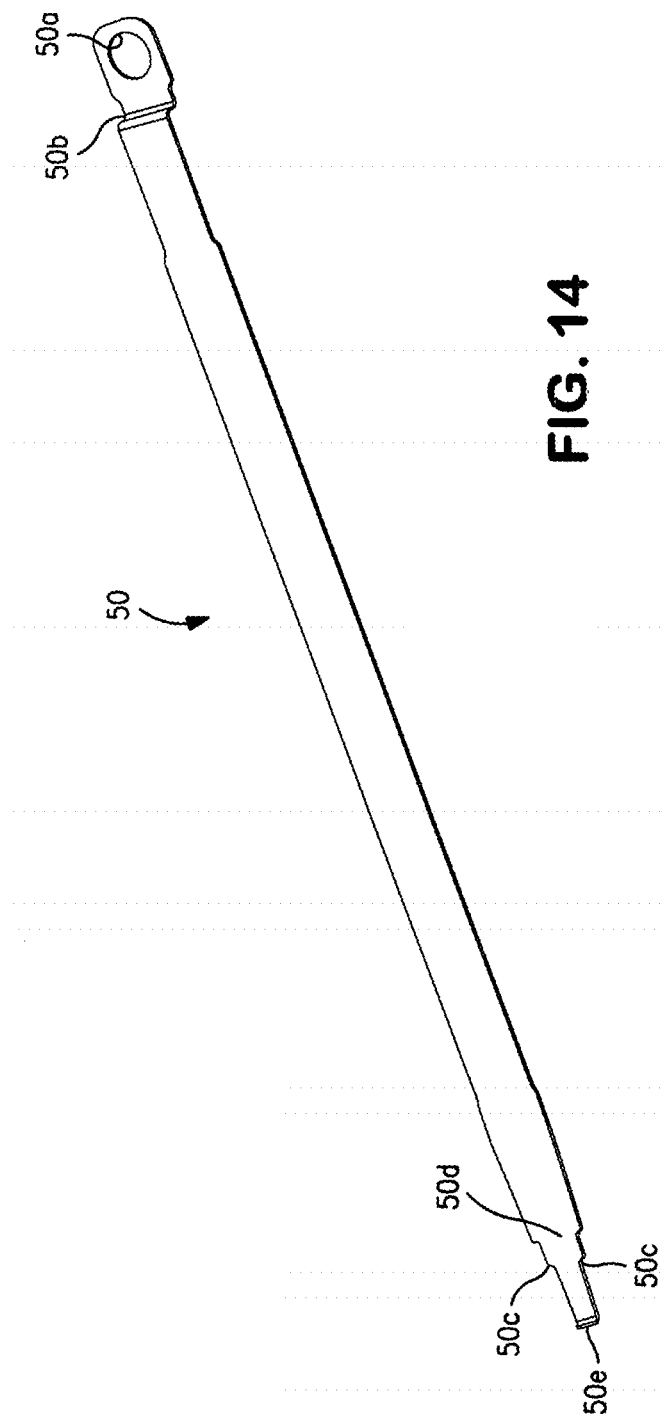

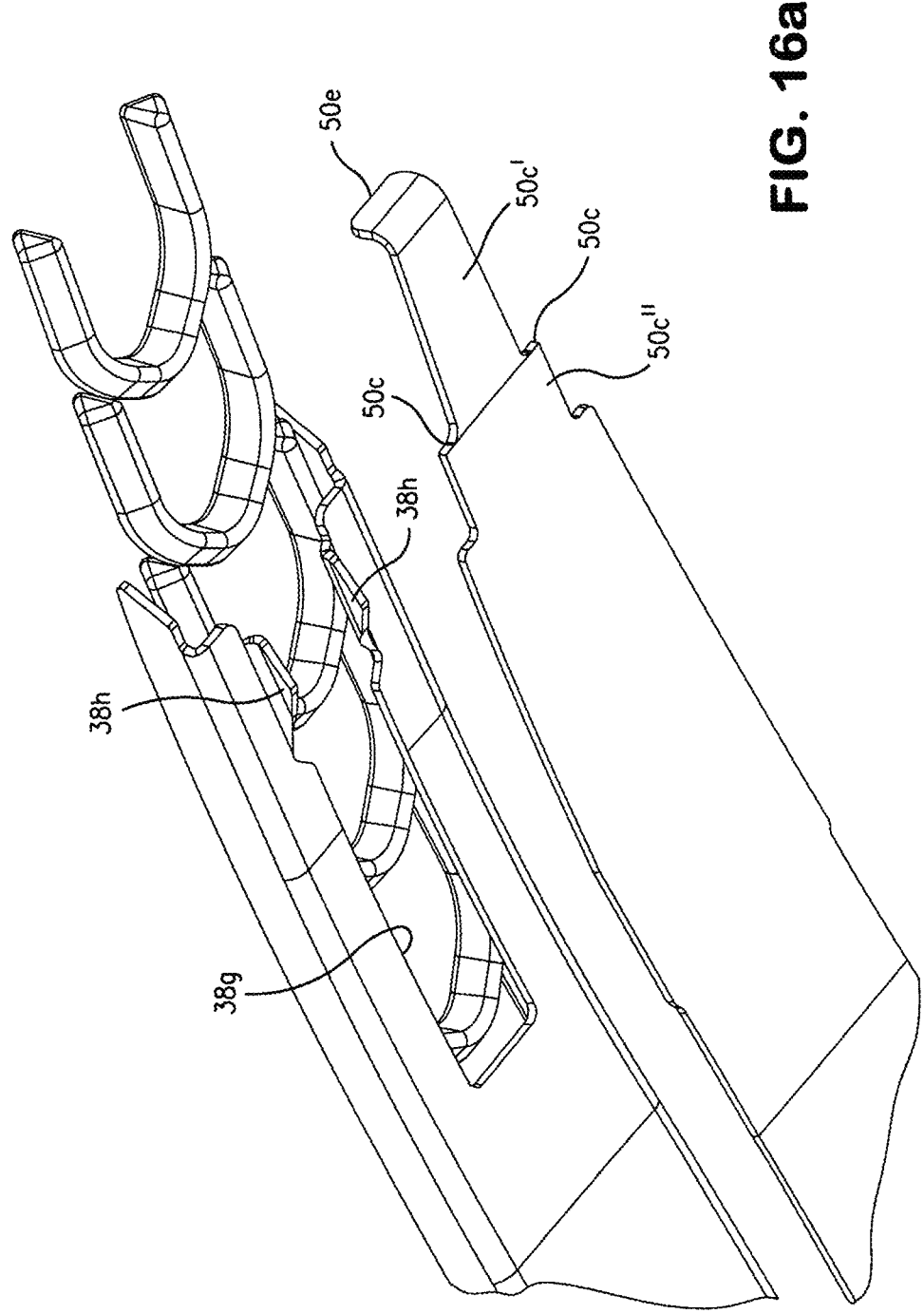

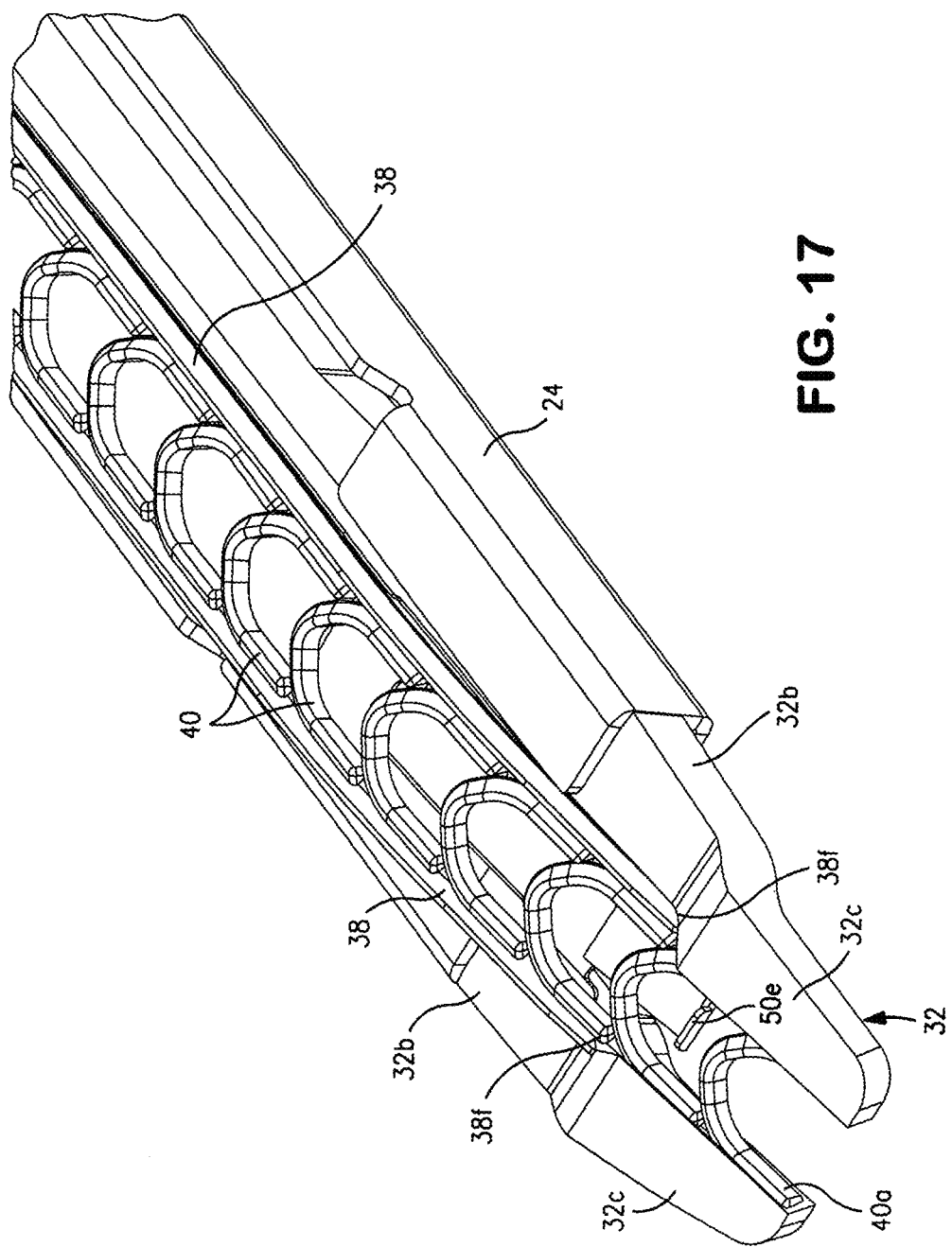

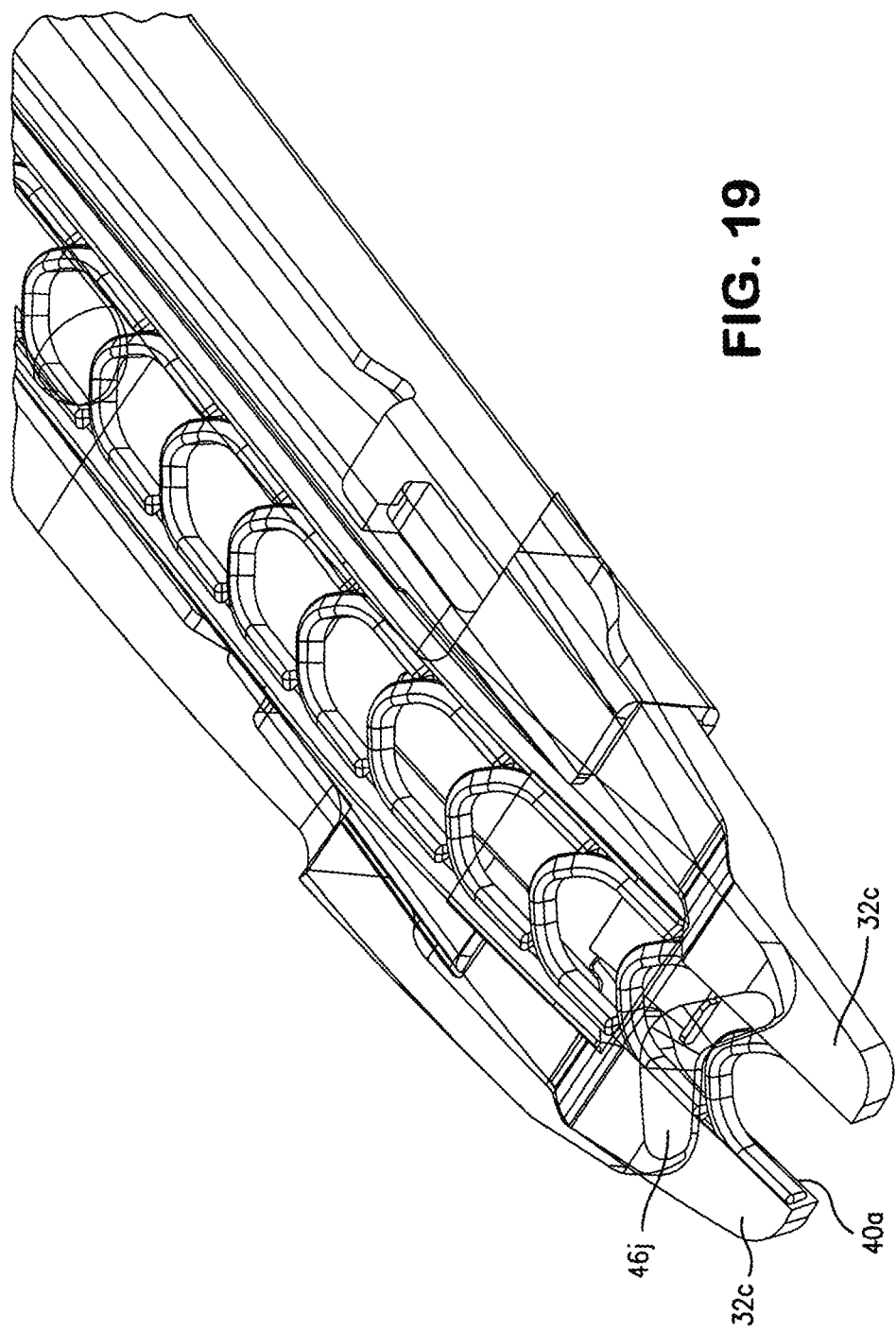

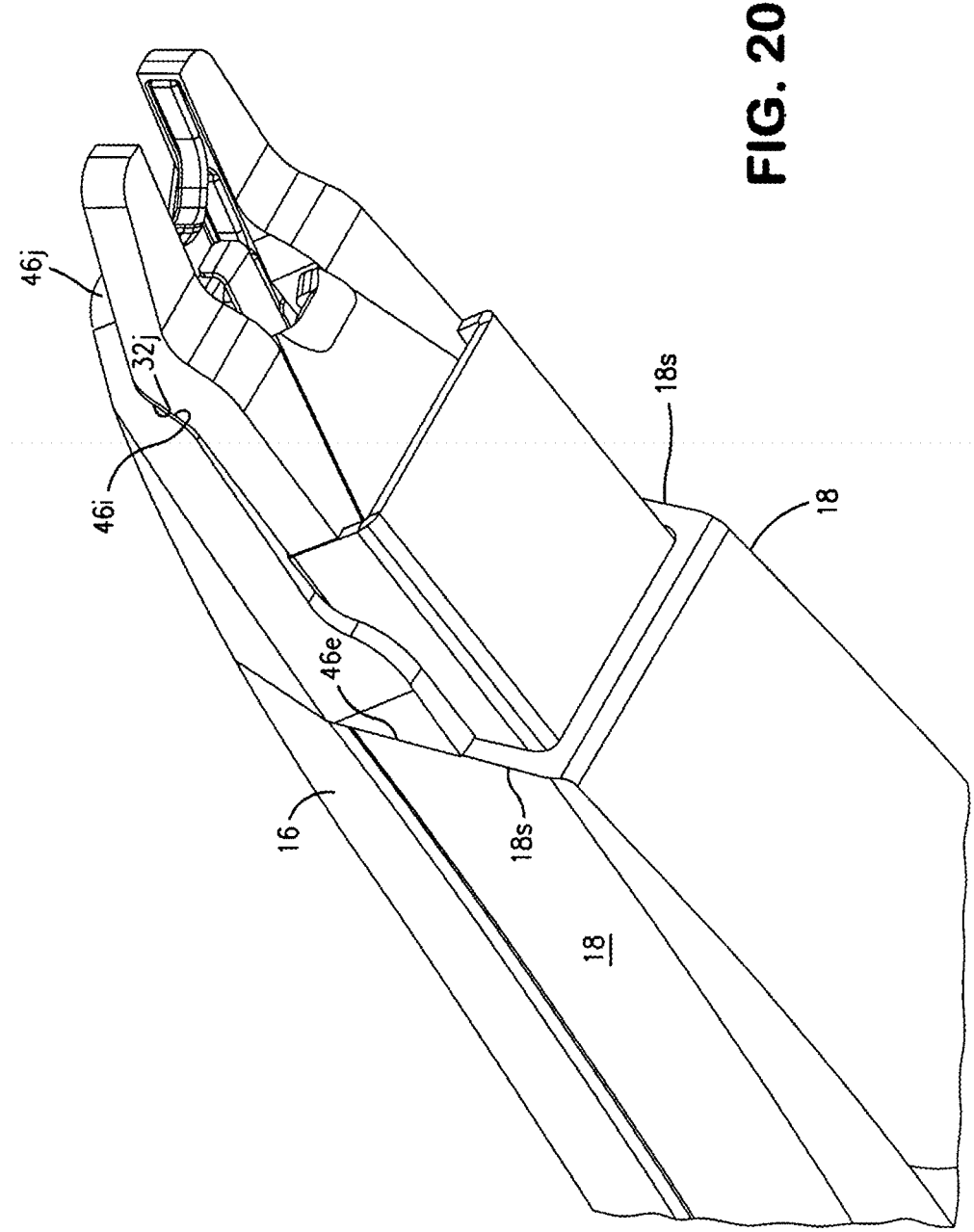

INSTRUMENT FOR SERIALLY APPLYING CLIPS TO A SURGICAL SITE

PRIORITY

This application claims priority of United States Provisional Application of Joseph W Blake III Ser. No. 61/962,661 dated Nov. 13, 2013 entitled A Medical Device for Serially Applying Clips to a Surgical Site the entire content of which is relied upon and fully incorporated herein by reference.

FIELD OF THE INVENTION

The present invention relates to clip appliers as an instrument having a supply of clips for closing blood vessels and other fluid carrying ducts in surgical procedures.

BACKGROUND OF THE INVENTION

A preferred embodiment of an instrument according to the present invention is particularly suitable for microsurgical procedures. Microsurgery covers a variety of procedures using a microscope for operating on successively smaller blood vessels, nerves, or other tubular members typically 1 mm in diameter. Microsurgical techniques are used for several surgical specialties including ear, nose and throat; reconstruction after resection of head and neck cancers; eye surgery; and reversal of vasectomies and tubal ligations. In reconstructive procedures such as perforated flap procedure, composite tissue is transferred as a free flap to the region requiring reconstruction and vessels supplying the free flap are anastomosed using microsurgery to matching artery and vein at the reconstructive site. For reattachment of a completely severed body part such as a finger or thumb, blood flow is restored through veins and arteries, bony skeleton is restored, and tendons and nerves are connected all using microsurgery.

Conventional suturing techniques in microsurgery have given way to the use of surgical clips applied at the junction of vessels or tissue parts to be joined where the clips perform a holding action akin to that of sutures. Hemostatic clips are used for tying off bleeding blood vessels in surgery and in traumatic medical intervention. Here a clip applier with opposed jaws crimps (or flattens) a U-shape clip over a blood vessel to close its lumen. These clips are also used to close other fluid ducts during surgery.

The clips used in microsurgery are very small and are called microclips. Microclips are typically fabricated of titanium alloy and have size on the order of 2 mm high and 2 mm wide. Herein, the term "microclip" is used in a very general sense. It includes metal staples or clips, but also surgical fasteners made of synthetic material and similar fasteners.

There are several manually operated instruments for applying microclips in a variety of microsurgical procedures including both open and laparoscopic surgery.

Microclips are commonly applied in surgery by forceps that load and use a single clip at a time. An attending nurse juggles several forceps which are individually reloaded from a disposable cartridge positioned on an instrument tray or elsewhere, e.g., adhesively attached to the nurse's wrist. Loaded and emptied forceps are alternately passed between nurse and surgeon during a procedure.

Notable disadvantages of forceps single clip instruments are potential handling accidents between attending nurse and surgeon including a clip or instrument; damaged instruments; misloaded and unloaded instruments; failure to perceive an unloaded instrument with resultant inadvertent severing of vein and hemorrhage; and accidental dropping partially closed clip into a wound; maintenance of multiple instruments requiring cleaning, repairing, sterilization, and restocking. In addition, when in use a surgeon must re-identify surgical site and stabilize the instrument with each hand-off.

Bruncke U.S. Pat. No. 7,264,625 describes the use and limitations of clip appliers for microsurgery with particular reference to Kirsch US patents, and clip appliers invented at US Surgical Corporation of Norwalk, Conn. and now marketed by Le Maitre Vascular, Inc as Anastoclip VCS Vessel Closure System. According to Bruncke, microsurgery, such as in plastic and reconstructive surgery, neurosurgery, replantation of limbs and appendages, hand surgery, endoscopic and arthroscopic procedures, often involves the need to suture or otherwise close wounds on extremely small tissues, including blood vessels of 2 mm external diameter and smaller. The very small vessels often need to be united or reunited together, in a procedure known as vascular anastomosis. Sometimes a large number of these anastomoses are required. In small vessels it is usually undesirable to employ suturing, because suturing invades the interior lumen of the vessel and can cause problems of restricting blood flow and promoting clotting in the lumen. For these reasons implements have been developed for applying very small non-penetrating clips to the walls of blood vessels. Some of these clips and application procedures are shown in Kirsch U.S. Pat. Nos. 4,586,503, 4,733,664 and 4,929,240. The VCS Clip Applier has three different sizes of stems, and of clips dispensed and secured by the tips of those stems, including a small size for microsurgery applications on vessels of 2 mm external diameter and under. The VCS Clip Applier is manual and one-handed in operation. When the clip is dispensed it is squeezed inwardly, deforming the clip to a smaller size. To do this the surgeon squeezes together two thumb/finger wings extending out from opposite sides of the tool's handle near the tip end of the handle; this squeezing motion is effective to slide a linkage piece in the stem, causing, at the tip of the stem, inward clamping and dispensing of the clip. In a longitudinal split or line of juncture on a blood vessel or between blood vessels to be joined, the VCS Clip Applier is used to apply the clips closely and accurately together for hemostasis. The clips are left in place and need not be removed.

Particularly in the smallest version of the VCS Clip Applier, useful on blood vessels of 2 mm in external diameter and smaller, there is a problem in maintaining the stem tip steadily in position while squeezing the wings of the handle to install a clip. This is done under the microscope, and often it is difficult to apply a clip accurately. Even if the surgeon has a very steady hand, the requirement of muscle contraction to squeeze inwardly on these handle wings almost inevitably causes some small movement at the tip of the clip applier stem, at the very instant of clip application. The result is an inaccurate application of clips.

U.S. Pat. No. 6,322,578 to Houle et al discloses endoscopic microsurgical instruments capable of using a clip applier for applying a surgical clip. Although multiple clips are applied in microsurgery, the clip applier disclosed by Houle has single clip capacity.

The present invention is directed to a surgical microclip applier for use in microsurgery that provides significant advantages over prior art instruments of the type described.

SUMMARY OF THE INVENTION

The present invention provides a microclip applier for microsurgery in which clips on the order of 2 mm high and 2 mm wide are used for hemostasis of blood vessels on the order of 1 mm diameter. An instrument according to the invention is used in appropriate surgical procedures primarily for closing off (ligating) fluid flow through conducting vessels. The instrument may be used for marking, tissue capture, suture retention or other creative applications that may occur to the operator during a procedure. The instrument is directed more specifically to application of microclips as used in microsurgery and plastic surgery applications.

The invention is a hand-held serially repeatable one-time use instrument delivered to user-surgeon pre-packaged and sterilized. The instrument is preloaded with clips to be delivered serially at a surgical site with each compression and release of its handles. The instrument eliminates surgeon distraction inherent in instrument-passing of single clip devices where the surgeon needs to re-identify surgical site and stabilize instrument with each pass. The invention results in greater speed and efficiency in surgical procedures with attendant cost advantages.

The invention integrates a handle together with clip handling and applying mechanisms so as to provide a unitary instrument that is held and actuated by one hand to perform a full instrument operating cycle through one squeeze and release of applier handle. The instrument includes a magazine containing a line of clips for application in series during a surgical procedure.

The instrument integrates operating handle with instrument housing of superimposed cover and chassis. The chassis carries jaws and actuating cam for applying clips, while cover carries line of clips and clip feeding components. Cover and chassis are joined for clip handling and applying operation. Instrument handles are integrated into housing of cover and chassis to provide operating motion to clip handling and applying components.

In a full instrument operating cycle, a microclip is applied in microsurgery and the clip applier jaws are reloaded with a single clip from a clip supply channel for clip application in the next cycle. The applier provides a clip supply channel containing a line of clips that are released seriatim.

Clip crimping jaws apply a clip with a rearward movement of a jaw cam member thereby allowing the functions of clip loading and jaw closure to be coordinated and operated by sliding cam bar and actuating bar moving reciprocally to load and fire clips.

The clip actuating mechanism includes a actuating bar and in-line clip supply channel working together so that with a squeeze of the operating handle, the actuating bar moves rearward in the instrument closing the jaws to apply a clip in surgery, a clip retractor linked to the actuating bar pulls the stack of clips rearward leaving the foremost clip in the jaws for individual closure around a blood (or other) vessel, and that with release of the operating handles, the jaws open, the next clip is loaded into the jaws, and the instrument is ready to apply another clip.

The instrument further comprises means to prevent clip dropping; an anti-backup mechanism to prevent a partial squeeze and release of the operating handles to avoid a well-known hazard that can occur when clip appliers are used in surgery; and a last clip lock-out means that guards against accidental empty jaw closure on a vein thus avoiding severing and hemorrhage.

In use, the instrument is held in the palm with handles in grip position between thumb and fingers. Positioning is flexible and relatively unrestricted. Guiding the tip of the instrument with an extended forefinger is a useful option for instrument stabilization. The jaw portion of the applier with clip in position is placed about the vein or tissue to be clinched and clip closure commences with the compression of the opposing handles. During the closing stroke, an anti-backup ratchet engages within the instrument and prevents clip release until the stroke is complete, an important feature to prevent partially closed clips from dropping into a wound. The anti-backup ratchet can also pause instrument handles in mid-stroke with a clip partially closed, enabling a surgeon to capture a vein in the partially closed clip and slide the clip along the vein to an optimally chosen location before final closure of the clip. When the clip closing stroke is complete, the handles are released allowing the jaws to open to receive a fresh clip fed from the magazine stack of spring biased clips. The instrument has now completed a full cycle and is prepared for continued actuation until exhausting the clip supply.

In practice, a microclip applier is ordinarily used a single time and discarded. The packaged clip applier is brought into the operating room and opened when needed. The instrument is passed on request to the surgeon who performs the procedure moving location to location at surgical site with minimal or no distraction until completion. A used applier is recorded in the instrument count and disposed of on-site.

Specific examples are included in the following description for purposes of clarity, but various details can be changed within the scope of the present invention.

OBJECTS OF THE INVENTION

An object of the invention is to provide a microclip applier for microsurgery.

Another object of the invention is to provide an instrument for handling and applying a line of microclips of a size on the order of 2 mm in both height and width.

Another object of the invention is to provide an instrument for crimping microclips over tissue ducts having a diameter on the order of 1 mm.

Another object of the invention is to provide an instrument of integrated handle and clip applying mechanisms having a full operating cycle realized by a squeeze and release of the handle.

Another object of the invention is to provide an instrument housing defined by cover and chassis which integrates operating handles with clip handling and applying components.

Another object of the invention is to provide an instrument held and actuated in one hand for applying a series of microclips in microsurgical procedures.

Another object is to provide a clip applying instrument limiting handle operation to full non-reversible pull and release strokes.

Another object of the invention is to provide an instrument capable of pausing handle movement in compression stroke for capturing a vein with a partially compressed clip, and for moving the clip along the vein to be clinched at optimal location.

Another object of the invention is to provide a lockout mechanism preventing further operation of the instrument after its last clip is used.

Another object of the invention is to provide a hand-held instrument with a stack of microclips, the instrument being pre-packaged and sterilized for one-time use for greater speed and efficiency in surgical procedures with attendant cost advantages.

Other and further objects of the invention will become apparent with an understanding of the following detailed description of the invention or upon employment of the invention.

BRIEF DESCRIPTION OF THE DRAWING

A preferred embodiment of the invention has been chosen for detailed description to enable those having ordinary skill in the art to which the invention appertains to readily understand how to construct and use the invention and is shown in the accompanying drawing in which:

FIG. 6b is an underside view of exterior configuration of the chassis of FIG. 6a.

FIG. 7b is a perspective view of interior configuration of the cover of FIG. 7a.

FIG. 11b is a bottom perspective view of a subassembly of jaws and cam bar illustrated in FIG. 11a.

FIG. 11d is bottom plan view of assembled jaws and cam bar of FIG. 11a.

FIG. 12 is a top perspective view of midsection of instrument of FIG. 1 with cover removed illustrating anti-backup components.

FIG. 12a is a perspective view of anti-backup mechanism pawl.

FIG. 14 is a top perspective view of clip retractor of instrument of FIG. 1.

FIG. 15b is a fragmentary underside perspective view of distal end of magazine of FIG. 15a.

FIG. 16a is an underside view of clip retractor of FIG. 14 and magazine of FIG. 15b.

FIG. 17 is a top perspective view illustrating clip line and clip path into jaws, together with frame, magazine, and clip retractor bar.

FIG. 18b is an inside perspective view of the magazine carrier lens of FIG. 18a.

FIG. 19 is a topside perspective view illustrating clip line and clip path into jaws, together with frame, magazine, and clip pullback bar with magazine carrier lens in place.

FIG. 20 is an underside perspective view of assembled components shown in FIG. 19 with chassis added.

FIG. 21b is an inside perspective view of the pusher spring cover of FIG. 21a.

DETAILED DESCRIPTION OF THE PREFERRED EMBODIMENT

Figure 1:
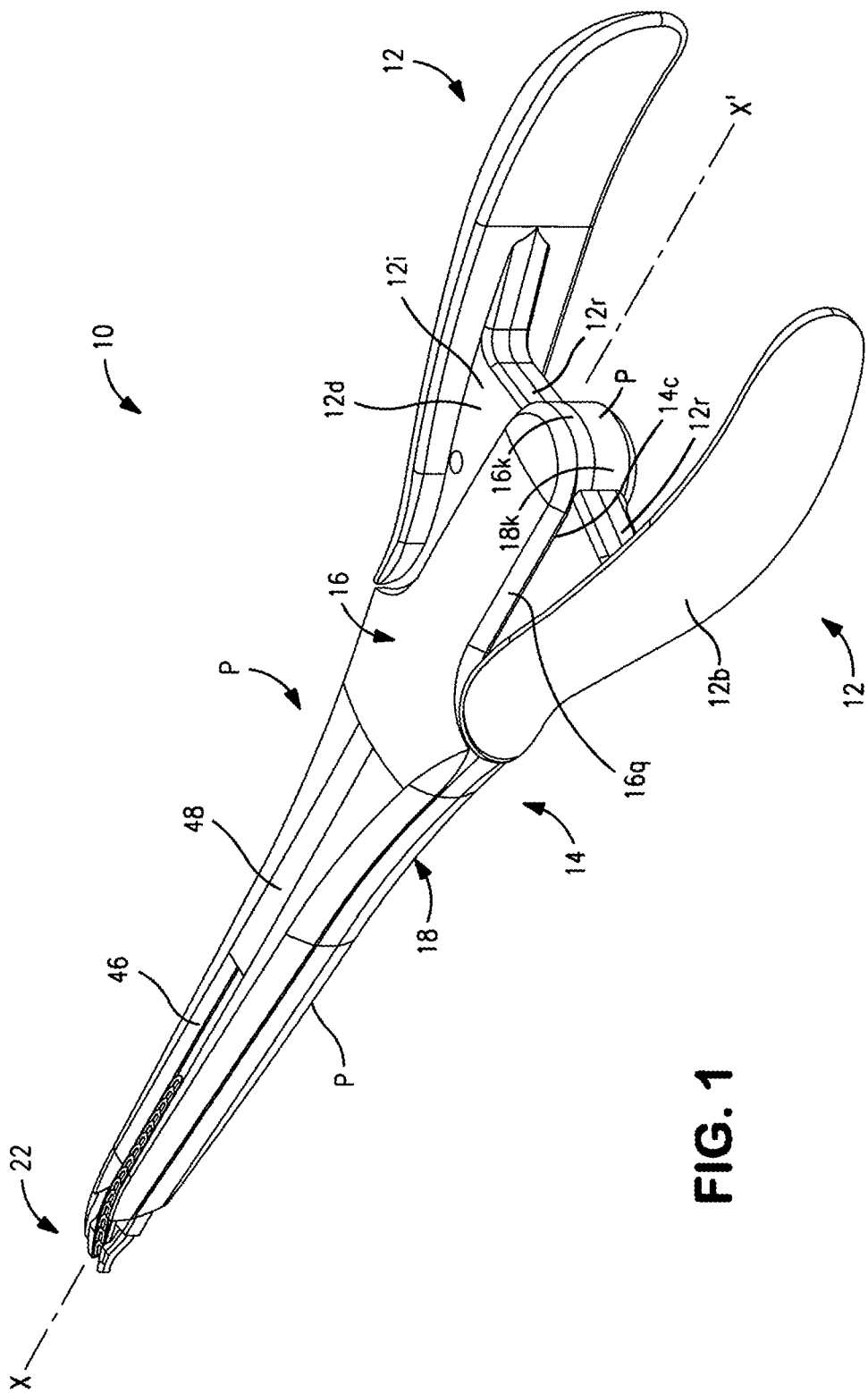
FIG. 1 is a topside perspective view of a preferred embodiment of an instrument for applying clips at a surgical site according to the invention.
Figure 2:
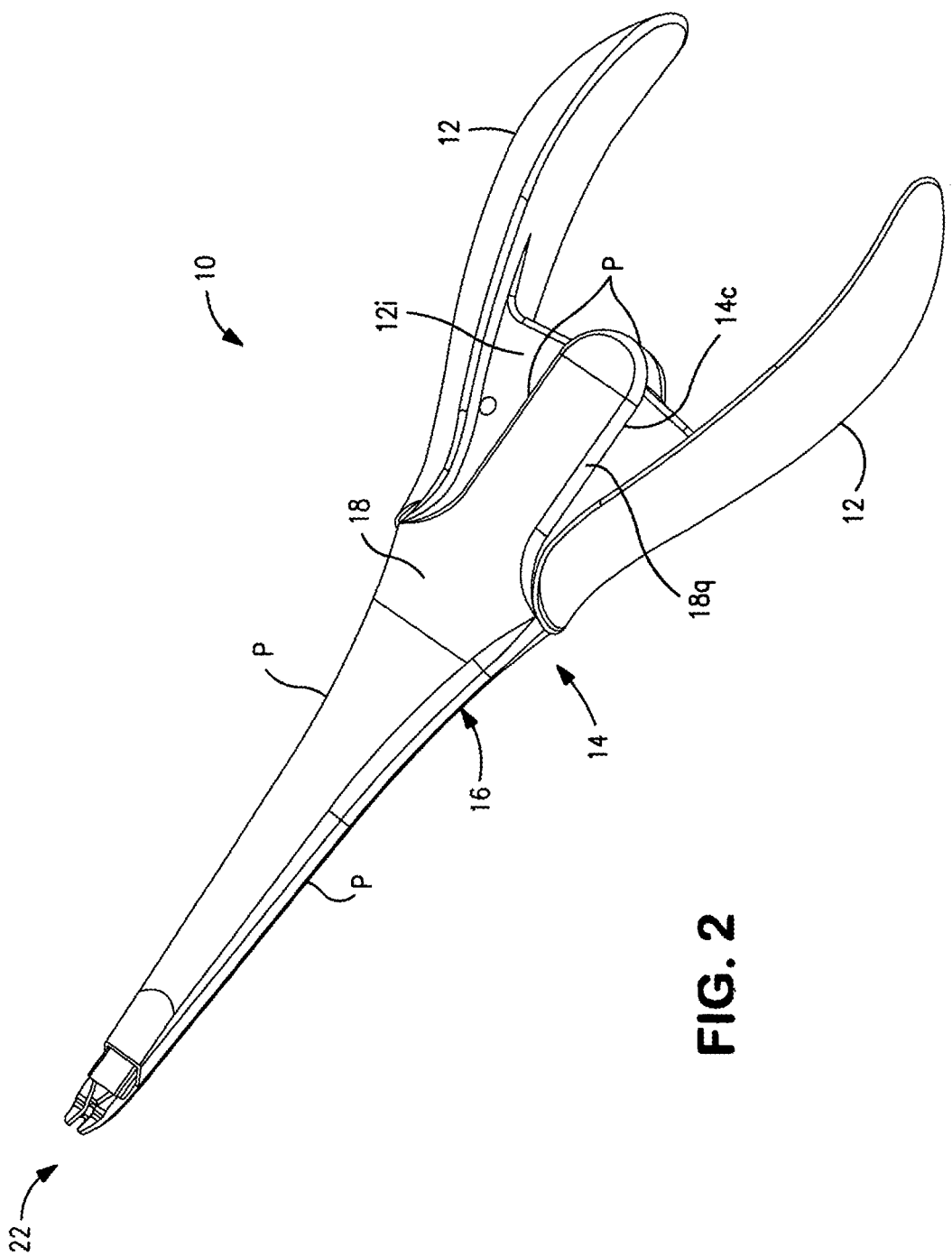
FIG. 2 is an underside view of instrument of FIG. 1.
Figure 3:
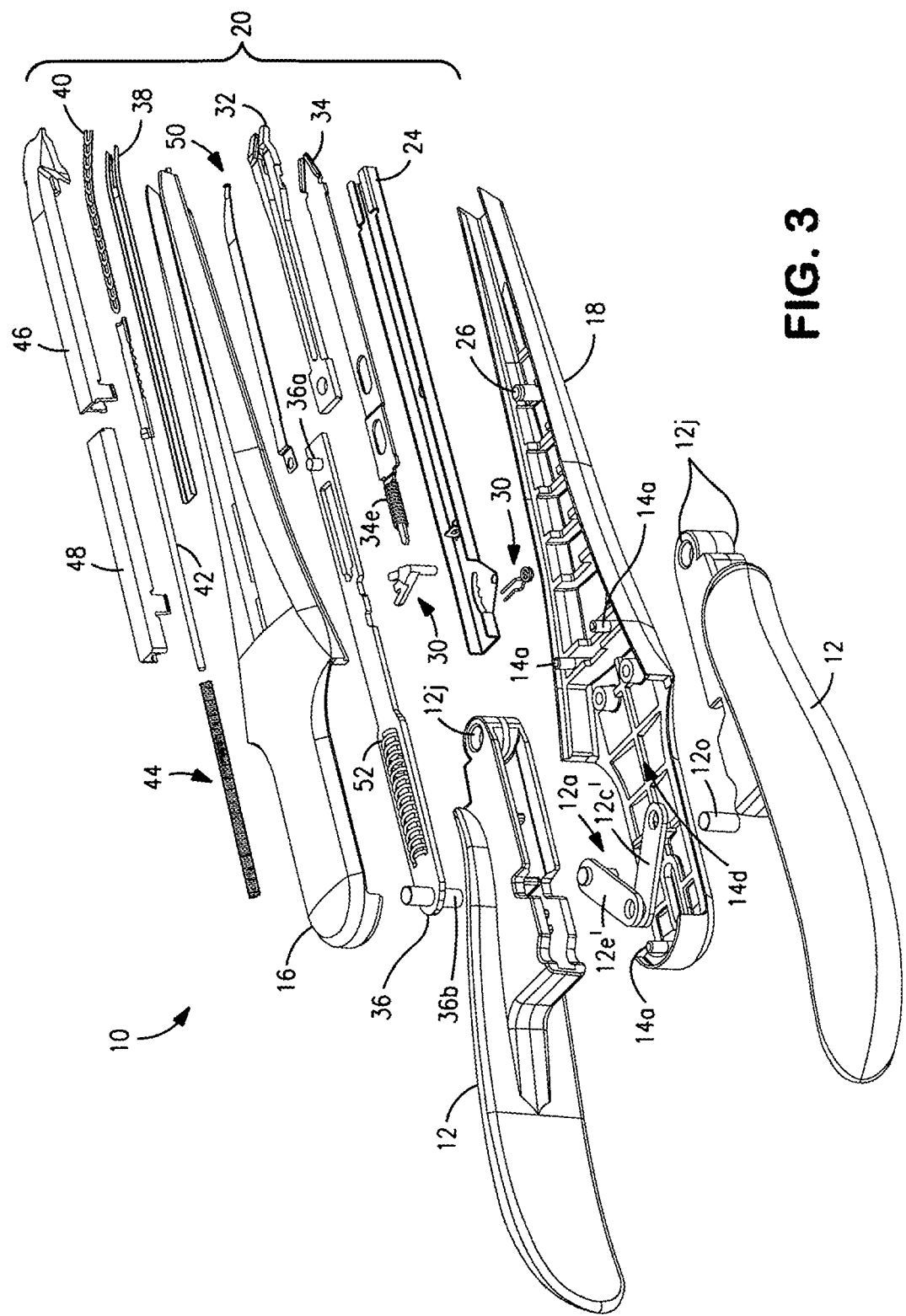
FIG. 3 is an exploded perspective view of the component parts of the instrument of FIG. 1.

Referring to drawing FIGS. 1-3, a preferred embodiment of instrument 10 for serially applying clips to a surgical site comprises handle arms 12 pivotally mounted on a housing 14 defined by cover 16 and chassis 18. The entire complement of instrument operating components 20 (FIG. 3) both for handling and applying clips in surgery, and for anti-backup and lock-out functions of the instrument are positioned within the housing.

The instrument housing comprises chassis and cover secured together by fasteners or other suitable means for manufacturing purposes. The chassis as well as the cover are fabricated of molded plastic.

The housing 14 is defined as an assembly of chassis and cover, with the housing having a perimeter P along outer edge where chassis and cover are joined. The chassis and cover define jaw point 22 at the perimeter where clips are applied. The chassis and cover handle section (FIGS. 6a-b, 7a-b) have floor 18d and ceiling 16c' respectively, front walls 18g, 16e at junction of handle section and instrument component section, and rear wall 18k, 16k spaced across handle section from the front wall. The rear wall defines a portion of the perimeter of the housing. The cover and chassis each have a pair of side walls 16q and 18q, respectively, extending along the perimeter from ends of the front walls 16f-g and 18e-f up to the rear walls 16k, 18k. Handle gaps 14c exist along perimeter P between side walls and between front walls and rear wall for access to interior chamber 14d for receiving handle lever arms 12 and linkage 12a (FIGS. 3-4) mounted within the chamber and extending through handle gaps 14c.

When assembled, the housing accommodates handle arms 12, linkage 12a between arms, and subassembly of instrument puller bar 36 and instrument return spring 52 (FIG. 4) which cooperate with handles in delivering linear reciprocating motion of fixed excursion to instrument operating components.

Cover and chassis form housing and place their respective clip applying components 20 (FIG. 3) in proper operating positions. The chassis positions frame 24, actuator or puller bar 36, cam bar 34, jaws 32, clip retractor 50, and anti-backup mechanism 30 for cooperation with clip handling components positioned by the cover. The cover positions clip handling components including magazine 38, clip stack 40, clip pusher 42, clip pusher spring 44, magazine carrier lens 46, and pusher spring cover 48.

Chassis 18 (FIGS. 2, 3, and 6a-b) comprises an elongate supporting base or floor 18a having an integral handle section 18b and instrument component section 18c. Handle section 18b has inner contour defined by ribbed plate 18d, front wall sections 18e-f-g, pivot pins 18h for handle arm pivot, instrument return spring stop 18i, handle link pin channel 18j, rear wall 18k and housing fasteners 14a. Instrument working components section 18c defined by side walls 18m converging from handle section 18b to jaw point 22, a set of interior generally parallel ribs 18n extending between side walls, the ribs being notched or recessed 18n' to define a central channel for accommodating a frame 24 (FIG. 3), a jaws retaining post 26, and a V-shape pillar 28 for an anti-backup mechanism 30 (FIG. 3). Pillar 28 (FIGS. 6a and 12) supports triangular extension 24e of frame 24. The inwardly facing V-notch provides space for pawl spring legs 30h (FIG. 13) to flex back and forth during operation. Pivot slot 28s receives pawl pin 30c (FIG. 12a) of the anti-backup mechanism as more fully described below.

Figure 6A:
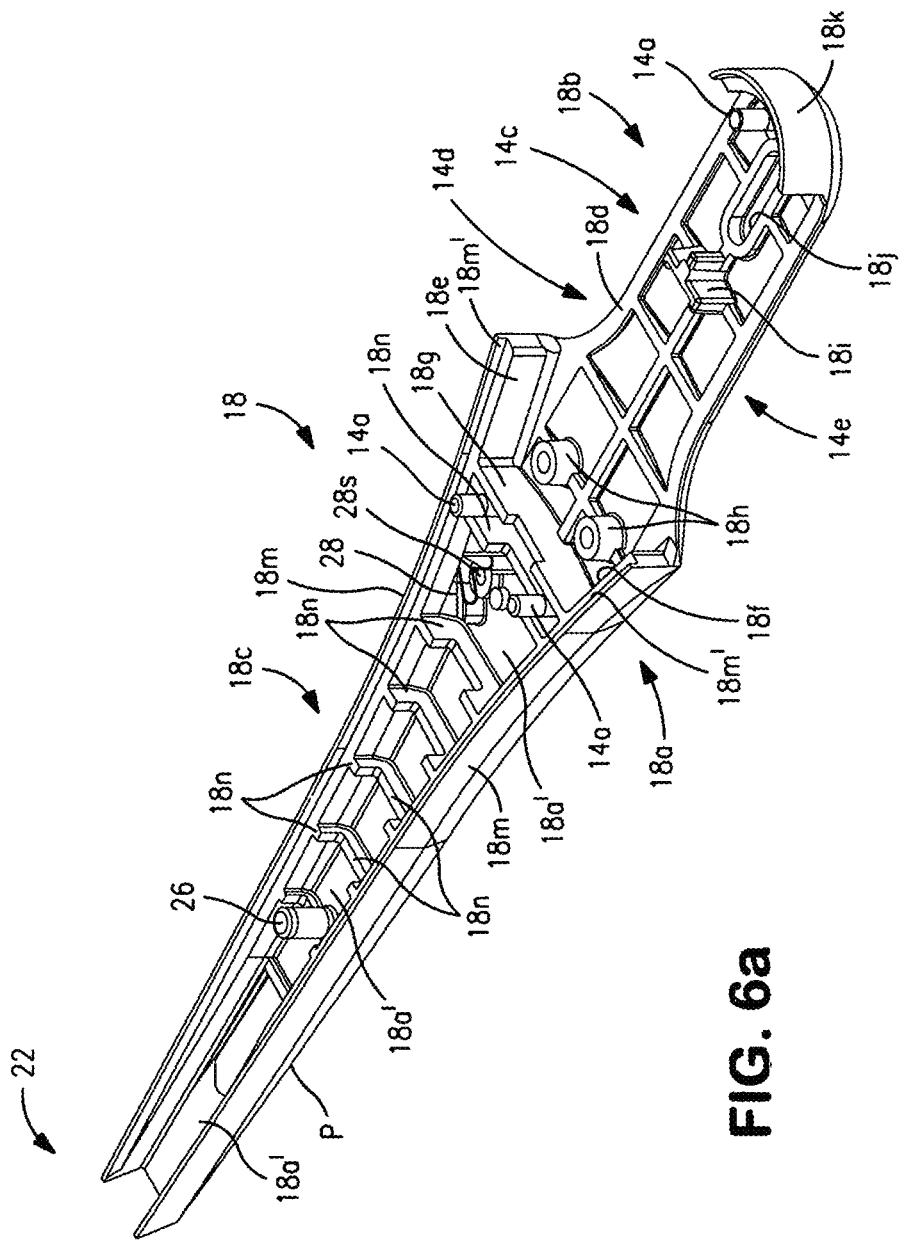
FIG. 6a is a topside perspective view of interior configuration of the chassis of the instrument of FIG. 1.
Figure 6B:
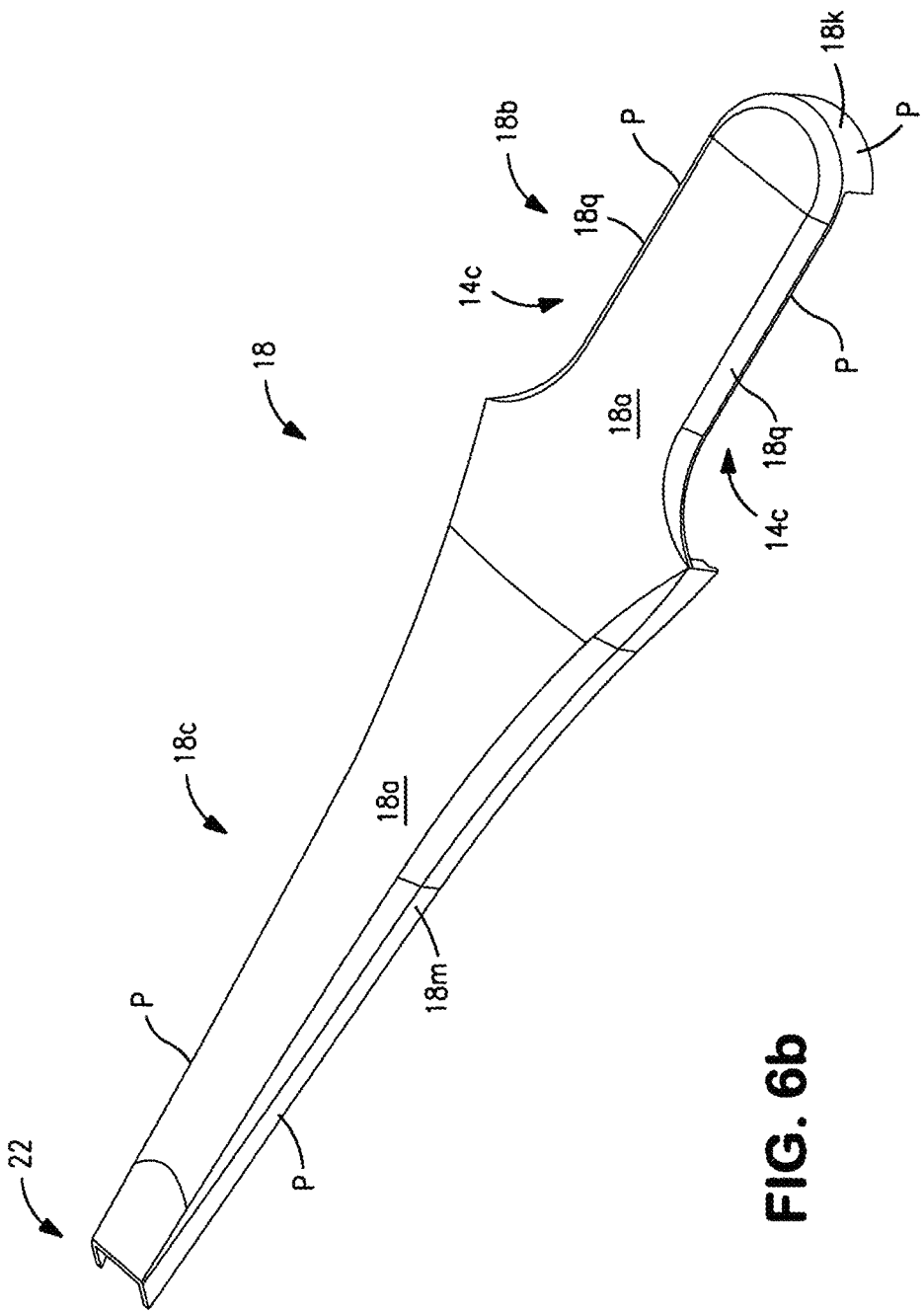

The chassis instrument component section is integral with handle section and is defined by sidewalls 18m extending along perimeter P from handle section sidewalls to jaw point. Sidewalls 18m have upwardly extending skirts 18m' for attachment to cover skirts 16m' as chassis and cover are secured to each other. A chassis set of ribs 18n with aligned notches 18n' define a channel above chassis flat 18a' extending from front wall 18g and converging along with side walls toward jaw post 26. The chassis channel further extends to jaw point 22 for receiving instrument operating components 20 including frame 24, jaws 32, jaws cam bar 34, and actuator bar 36. Jaw post 26 is located in the chassis channel. The chassis is recessed 28 to accommodate instrument anti-backup components 30. As best shown in FIG. 6a, chassis bottom wall 18a' extends from handle section converging to jaw point with distal portion of wall inclined to jaw point.

The cover 16 (FIGS. 1, 3, and 7a-b) comprises an elongate plate having integral handle section 16a defined by level surface 16c', return spring stop 16i, groove for linkage pin 16j, rear wall 16k, and fastener points 14b; and clip handling section 16b defined by top surface 16c and side walls 16m converging from handle section to jaw point, a central channel 16n in top surface from handle section to jaw point, and marginal skirts 16m' for connection to the chassis. The cover has centrally located slot 16o for accommodating reciprocating movement of actuator bar/cam bar pin 36a. The cover is also provided with recess 16p to receive chassis jaw post top portion.

The cover comprises an elongate plate having handle section 16a defined by top wall cover 16c and clip handling section 16b integral with the handle section. The clip handling section is defined by side walls 16m converging from handle section 16a to jaw point 22, downwardly extending skirts 16m' for attachment of side walls 16m to the chassis side walls 18m, an upwardly open central channel 16n from handle section to jaw point, a slot 16o for actuator bar pin 36a and for access of retractor bar 50 into cover channel 16n, an aperture 16p for jaw post 26, retaining slots 16q and 16r for carrier lens 46 and pusher spring cover 48, respectively.

The cover handle section 16a has inner contour (FIG. 7b) defined by flat ceiling 16c' (which may be ridged 16d), front wall sections 16e, and side walls 16f-g (contiguous with side walls 16m), pivot pins 16h for handle levers, return spring stop 16i, link pin channel 16j, rear wall 16k, and receptors 14b for housing fasteners 14a located on the chassis.

The cover instrument component section is integral with handle section and is defined by sidewalls 16m extending along perimeter P from handle section sidewalls 16f-g to jaw point, and by instrument component top wall 16c. Top wall converges along with sidewalls to jaw point. Cover channel 16n in top wall is approximately parallel to chassis channel and extends to jaw point for receiving instrument operating components 20 including clip magazine 38, line of clips 40, clip pusher 42 and spring 44, magazine lens 46, and pusher spring cover 48.

Clip retractor 50 is one of the clip handling components and is actuated through its connection to actuator bar pin 36a (FIG. 3).

The handle (FIGS. 1-5) comprises cooperating handle arms 12 for imparting linear reciprocating movement to the instrument interior operating components, and for receiving from return spring 52 included in the interior components a biasing force urging the handle arms to "open" position. Each handle arm has an arcuate lever body 12b, a loopless ergonomic configuration for gripping surface 12c along the outer side of the lever body, and an integral pier 12d extending inwardly and forwardly from the middle of the inner side 12e of the lever body. The outer surface 12b of lever body is over-molded with a rubber-like material providing for stable, firm, and comfortable gripping and handling of the instrument. Outer surface has a ridge line 12f convex in conforming to inside surface of a thumb to where it adjoins the palm, the outer surface being of variable convexity from opposite side perimeter 12g lines across median ridge line 12f, with the ridge line 12f' changing from convex to concave as it nears the front perimeter line 12h to define a thumb rest. Thus configured, the lever body outer surface provides a full, comfortable, fixed gripping surface for manual operation. The outer surfaces of handle arms are identical so instrument is easily turned over in the hand to advantageously allow alternate jaw angles at point of clip application.

Each pier 12d comprises a block with planar upper and lower surfaces 12i enabling the pier to slide in and out of handle gap openings 14c into the handle chamber 14d formed within housing of assembled chassis and cover. Upper and lower pivot recesses 12j are situated at corresponding pier forward surfaces and register with aligned pivot pins of chassis (18h) and cover (16h) within the housing chamber. The handle arms have their pivoting movement in cooperation of pivot pins and recesses. If desired for ease of manufacture, pins and recesses for pivoting handle arms can be reversed with recesses located on cover and chassis and pins located on handle pier surfaces.

The inner surface 12k of each pier is recessed laterally in two places at 12m and 12n to permit handle lever arm closing movement to full squeeze position. Recesses 12m provide clearance for spring stops 16i and 18i of the cover and chassis respectively against which return spring is compressed when handle arms are in closed position. Recess 12n provides working space for puller bar pin 36a with handle arms in closed position.

Figure 4:
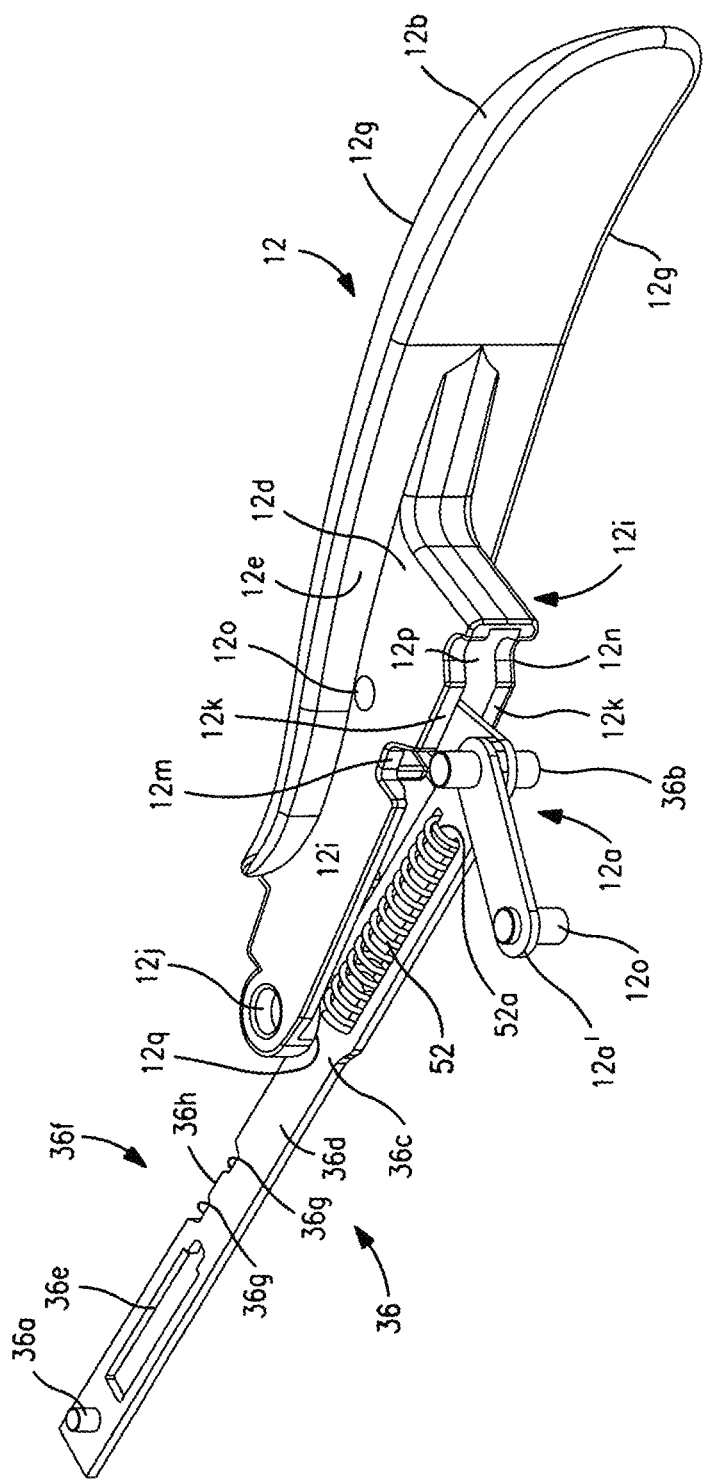
FIG. 4 is a perspective view of subassembly of one handle arm, together with linkage, and puller bar of the instrument of FIG. 1.
Figure 5:
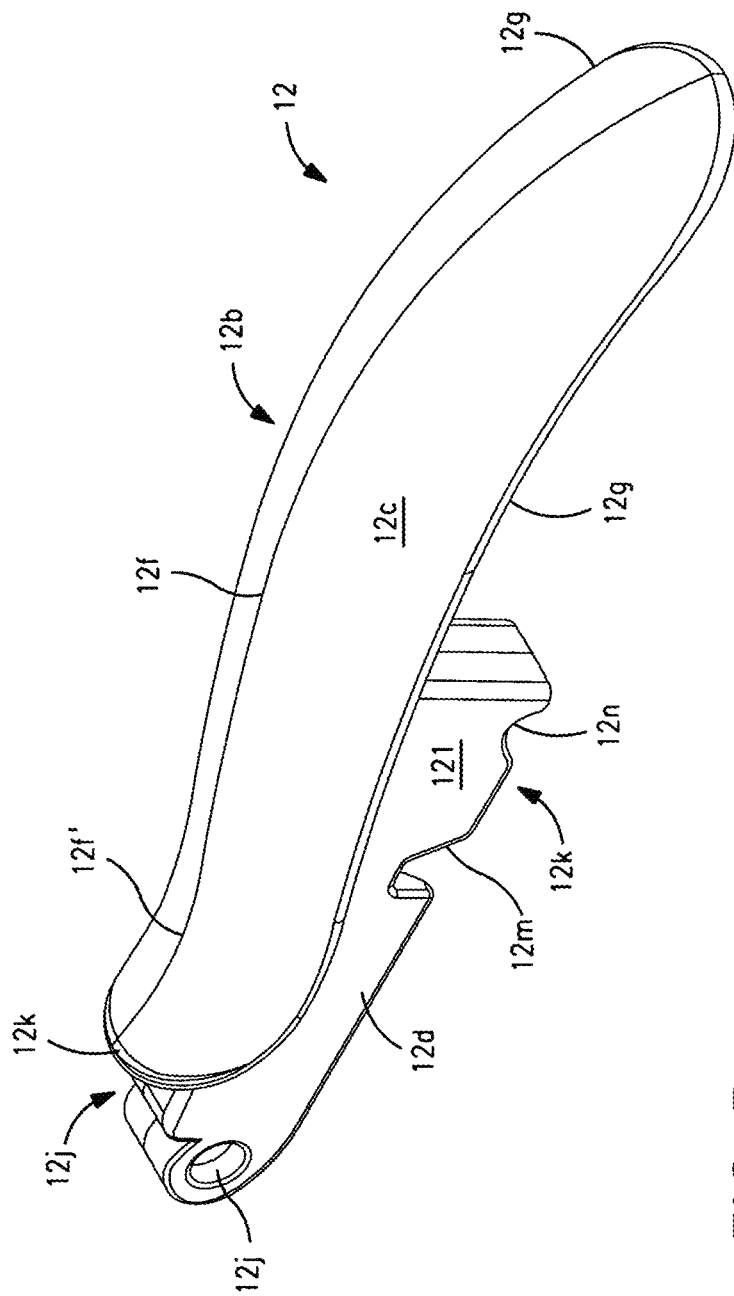
FIG. 5 is a perspective view of a handle arm of instrument of FIG. 1.

The inner surface of each pier is also recessed longitudinally in two locations to include a link bar recesses 12p for receiving toggle links 12a when the handle is closed, and a puller bar recess 12q to receive and accommodate the puller bar 36 during handle pull and release strokes. It is seen in FIG. 4 that recessed distal portion of both piers continually supports puller bar 36 mid-section 36c in sliding movement throughout handle operation. The return spring 52 is also accommodated at this location between handle arms. It is further seen in FIG. 4 that puller bar 36 is in forward-most (distal) operating position.

A toggle link 12a is formed by joining a pair of link bars 12a' each having a link pin aperture and a puller bar pin aperture. The bars are joined to pivot on puller bar pin 36b, and are secured by respective handle link pins 12o located within recesses 12p of the piers. The toggle link is moved by the handle members such that the puller bar pin undergoes a linear movement along housing axis X-X' and in so doing provides linear reciprocating motion of fixed excursion to puller bar as the handle moves from open-to-closed-to-open position. When handle is in closed position, aligned puller bar pin recesses 12n in each pier accommodate the puller bar pin.

Chassis and cover flats (FIGS. 6a-7b) are provided with cooperating puller bar pin channels 18j and 16j respectively to maintain pin 36b in axial position as it moves in operation.

Chassis and cover flats are provided with cooperating return spring stops 18i and 16i having distal faces to engage upper 52a and lower 52b runs (FIG. 8) of spring end coil above and below the puller bar surface to compress the spring when the handle arms are squeezed and the linkage draws the puller bar proximally. Return spring stop proximal faces form dihedral conforming to linkage angle.

Chassis and cover arcuate rear walls 18k, 16k come together to close rear end of housing chamber, and together have front edges clear of moving handle pier surfaces 12r (FIG. 1). Suitable fasteners 14a, 14b are formed on chassis and cover within the rear wall.

Referring to FIGS. 3, 4, 8, 9, 10, and 11a-b internal instrument components 20 carried in the chassis include frame 24, cam bar 34 and cam return spring 34a, jaws 32, anti-backup mechanism 30 of pawl 30a and pawl spring 30b, puller bar 36, return spring 52, and clip retractor 50.

Frame 24 preferably fabricated as a metal stamping comprises an elongate channel 24a of base plate 24b, parallel side walls 24c, a side wall breach 24d with triangular extension 24e of base plate defining both a pawl mounting aperture 24f and an arcuate anti-backup rack 24g, a cam return spring stop shoulder 24h stamped out of the base, an aperture 24i for jaw post 26, and fold-over top flanges 24j at jaw point 22.

The frame fits into and occupies chassis channel formed by notches 18n' (FIG. 6a) and extends from handle section wall 18g to jaw point, with frame triangular extension 24e supported by chassis V-shape recess 28. The triangular extension and chassis recess together with pawl 30a, pawl spring 30b, and rack 24g form anti-backup mechanism in cooperation with puller bar 36, the operation of which is detailed below.

Jaws shown 32 in FIGS. 8 through 11a-d comprise base plate 32a with jaw spring arms 32b extending in parallel from the base terminating in cooperating jaw heads 32c. The base plate has aperture 32d for securing the jaws to jaw post 26 of the chassis.

Jaw heads 32c have jaw steps 32j locating jaws above arm surface 32j' with jaws canted downwardly for establishing entry points 32e where clips move into jaws. The jaw heads have confronting inner surface clip grooves 32f for receiving open clips delivered by clip handling mechanisms. The jaw arms have a natural spring bias to jaw-open position and are forced closed by cam-bar ramps 34b engaging cam grooves for crimping a clip in surgery.

The under surfaces 32b' (FIG. 11c) of each spring arm have cam grooves 32e extending diagonally across spring arms converging toward jaw heads. Cam grooves are defined by spaced proximal 32g and distal 32h cam walls extending diagonally across jaw arms. Each proximal wall turns toward arm inner surface 32k to define a crowned point or edge 32i for engaging the cam bar ramps 34b. Crowned point 32i concentrates force from cam bar ramp 34b at a fixed location such that the mechanical advantage between cam and ramp does not negatively shift as cam bar 34 moves proximally to close the jaws. The distal walls 32h are provided with relief notches 32j between distal wall midpoint 32h' to jaw arm outer surface 32m. The relief notches prevent a binding condition when jaw arms flex to closed position of jaws.

Jaws 32 overlie cam bar 34 that receives linear reciprocating motion from puller bar 36 wherein cam bar moving proximally cams close jaws as part of operating sequence of instrument components. When cam bar moves distally, jaws spring open. The fold-over frame flanges 24j situated at jaw point rigidly constrain the interaction of jaws and cam bar preventing their disengagement, while maintaining the clip holding jaw heads in parallel configuration.

Frame 24 receives cam bar 34 shown in FIGS. 3, 8-10 overlying frame base with cam bar distal slot 34c fitting over chassis jaw post 26, and proximal slot 34d cooperating with cam bar pull pin 36a carried by puller bar. Cam bar 34 comprises an elongate body plate 34e with distal oval slot 34c on jaw post allowing sliding movement of cam bar with respect to stationary jaw post, frame, and jaws. Proximal oval slot 34d registers with puller bar drive pin 36a by which the cam bar receives reciprocating motion from the puller bar. The oval slots provide a delayed action of cam bar in instrument component operation to allow clip stack to clear jaws before jaws close to crimp a clip at a surgical site. During delayed action retractor bar 50 engages and moves clip stack to proximal leaving a clip in the jaws to be crimped, as described in detail below.

The cam bar has an up-step 34f between slots 34c and 34d to elevate proximal portion toward puller bar, and its spring tang 34g above frame base 24b so as to make room for free movement of cam return spring 34a. The spring tang 34g is formed integral with cam bar defining spring shoulders 34h at the tang base. Cam return spring fits onto the tang, and when cam puller bar and frame are assembled, the spring is held in place between cam bar shoulder 34h and frame spring stop shoulder 24h. The frame shoulder has an interior slot 24h' to receive spring tang as it slides through the shoulder for compressing the cam bar spring in operation as more fully described below.

The frame (FIGS. 3 and 8) receives the puller bar 36 carrying puller bar drive pin 36b, return spring 52, and cam bar pull pin 36a. The puller bar comprises an elongate plate 36d through which reciprocating motion developed by handle arms is received through pin 36b and distributed to instrument operating components including both cam bar 34 and clip crimping jaws 32, as well as clip retractor mechanism 50 which ensures that clips are fed one by one into the clip crimping jaws for each cycle of the clip applier. The puller bar serves as secondary mover for internal instrument operating components in that it receives linear reciprocating movement from prime mover instrument handles and transmits movement to operating components.

The cam bar pull pin 36a is carried in an aperture at distal end of puller bar projecting down into proximal cam bar slot 34d for pulling the cam bar and closing instrument jaws. Pull pin 36a projects upward to link with aperture 50a in clip retractor 50 for retracting clip line as described below. Puller bar slot 36e provides space and side constraint for cam bar return spring 34a.

Puller bar (FIGS. 4, 8) has anti-backup edge 36f of spaced notches 36g on either side of ratchet 36h having teeth which cooperate with pawl 30a and pawl spring 30b (FIG. 9) as detailed below. The puller bar extends toward the proximal end of frame and is widened at 36i to receive and position instrument return spring 52 in an H-shape slot 36j with opposed long 36k and short 36m tangs projecting within spring coil. The spring urges instrument components including handle arms to normal open starting position. The widened puller bar end lies within the handle section of the housing with puller bar pin 36b connected to the handle toggle link 12a.

Return spring stops 18i and 16i of chassis and cover flats engage return spring above and below the puller bar surface to compress the spring when the handle arms are squeezed and the linkage draws the puller bar proximally. The spring is fully compressed when handle arms are fully closed whence the spring urges puller bar and instrument to open position, as the handle arms are released.

Puller bar drive pin 36b is assembled with handle linkage, tracks in confronting chassis 18j and cover 16j slots, and receives linear reciprocating motion from handle arms for delivery to puller bar and instrument components.

The side edge of puller bar 36 (FIGS. 12, 13) mid-way along its length includes spaced edge notches 36g and ratchet teeth 36h extending between the notches as part of instrument anti-backup mechanism 30 that also comprises triangular frame extension 24e of base plate defining both a pawl mounting aperture 24f, an arcuate anti-backup rack 24g in frame base, pawl 30a, and pawl control spring 30b. As shown in FIGS. 3, 8, 9, 10, 12, 12a, and 13 pawl pin 30c fits through frame pawl aperture 24f and into chassis pivot socket 28s (FIG. 6a). Pawl control spring 30b fits onto pawl post 30c between the frame and chassis socket and is there held in assembly. The pawl 30a (FIG. 12a) comprises main plate 30d surmounted by pawl head 30e, centered pawl edge 30f, and centering post 30g with outwardly directed flanges 30g' depending from main plate.

Figure 13:
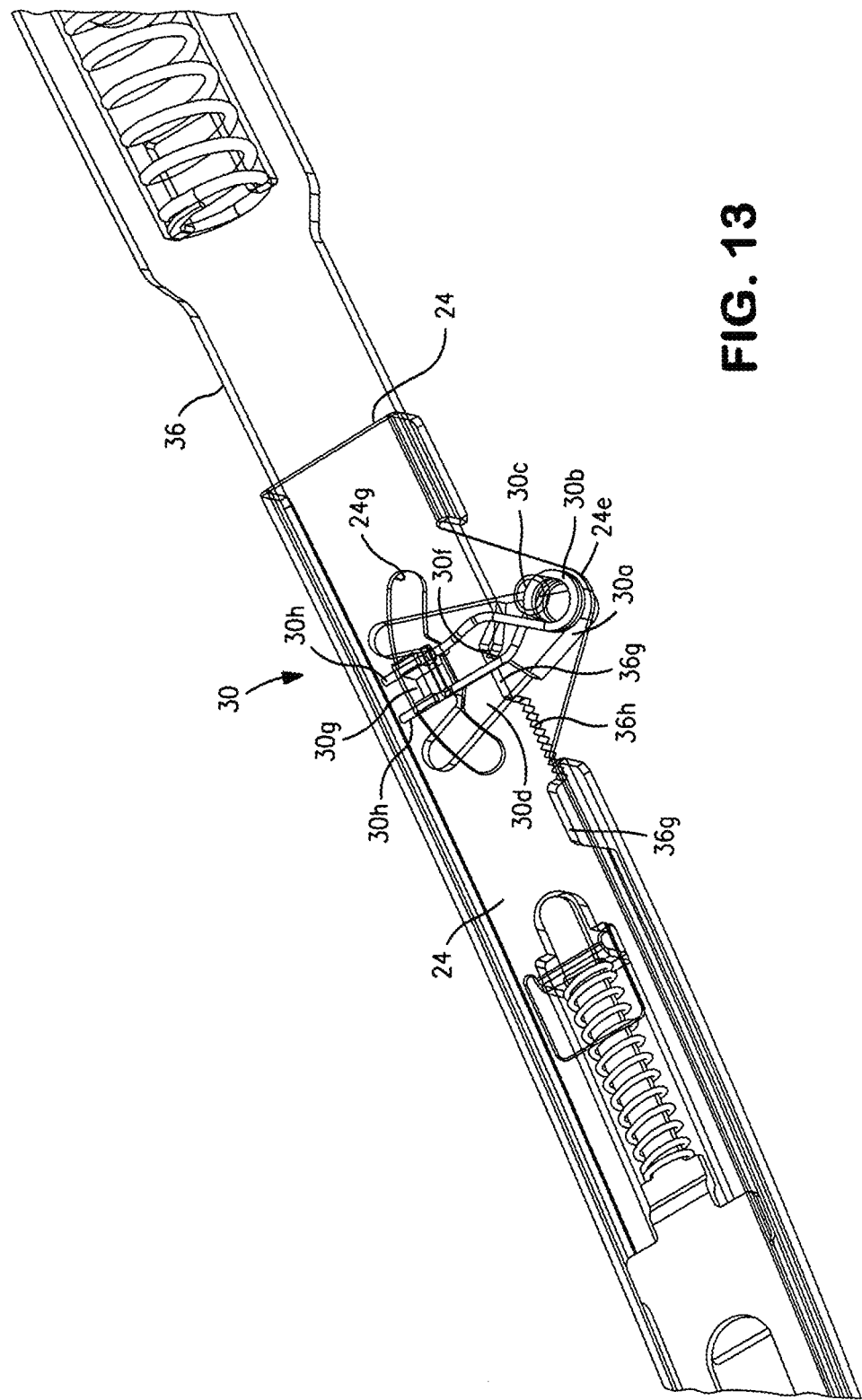
FIG. 13 is a bottom perspective view of midsection of instrument of FIG. 12 illustrating anti-backup components.
Figure 15A:
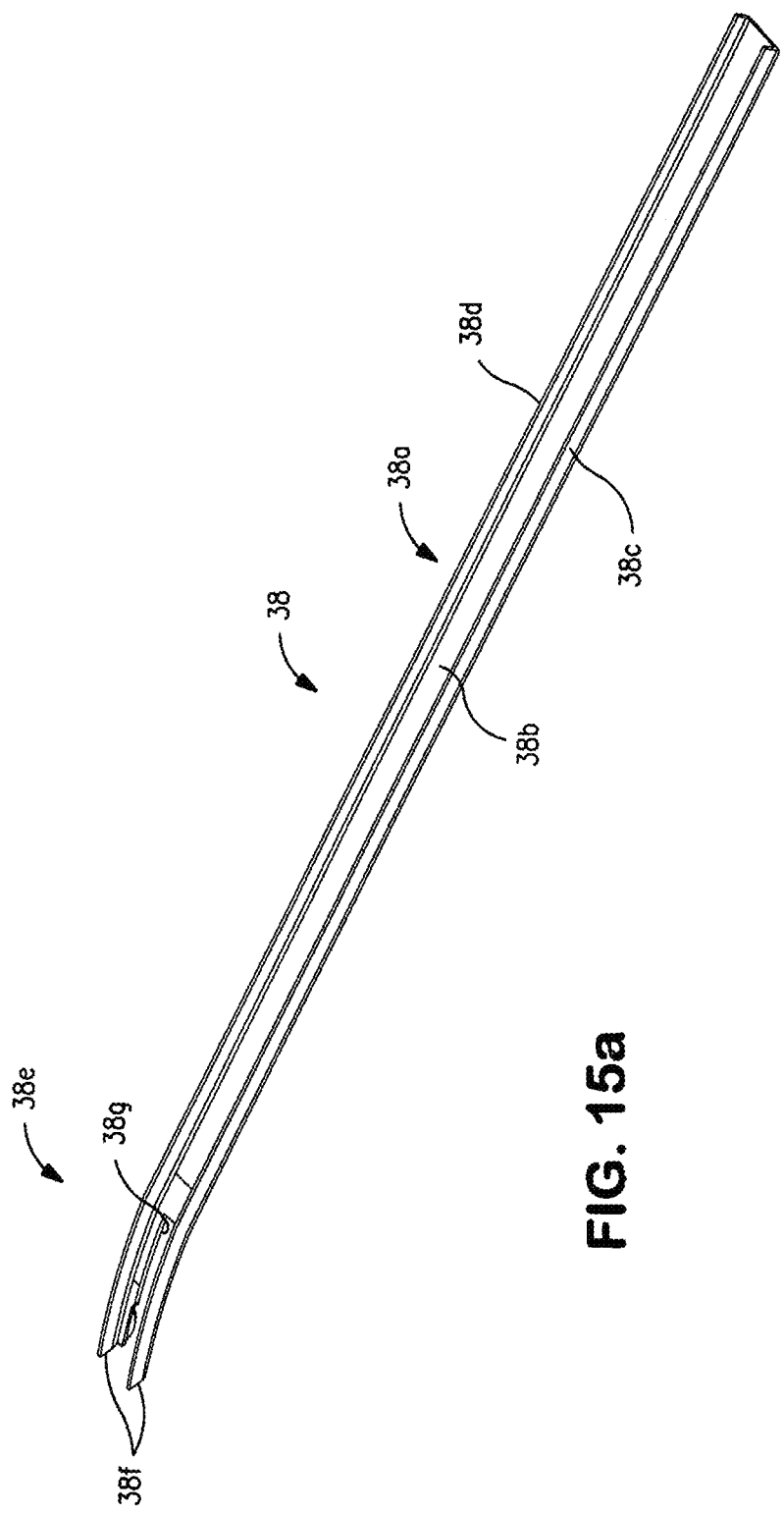
FIG. 15a is perspective view of magazine of the instrument of FIG. 1.
Figure 15B:
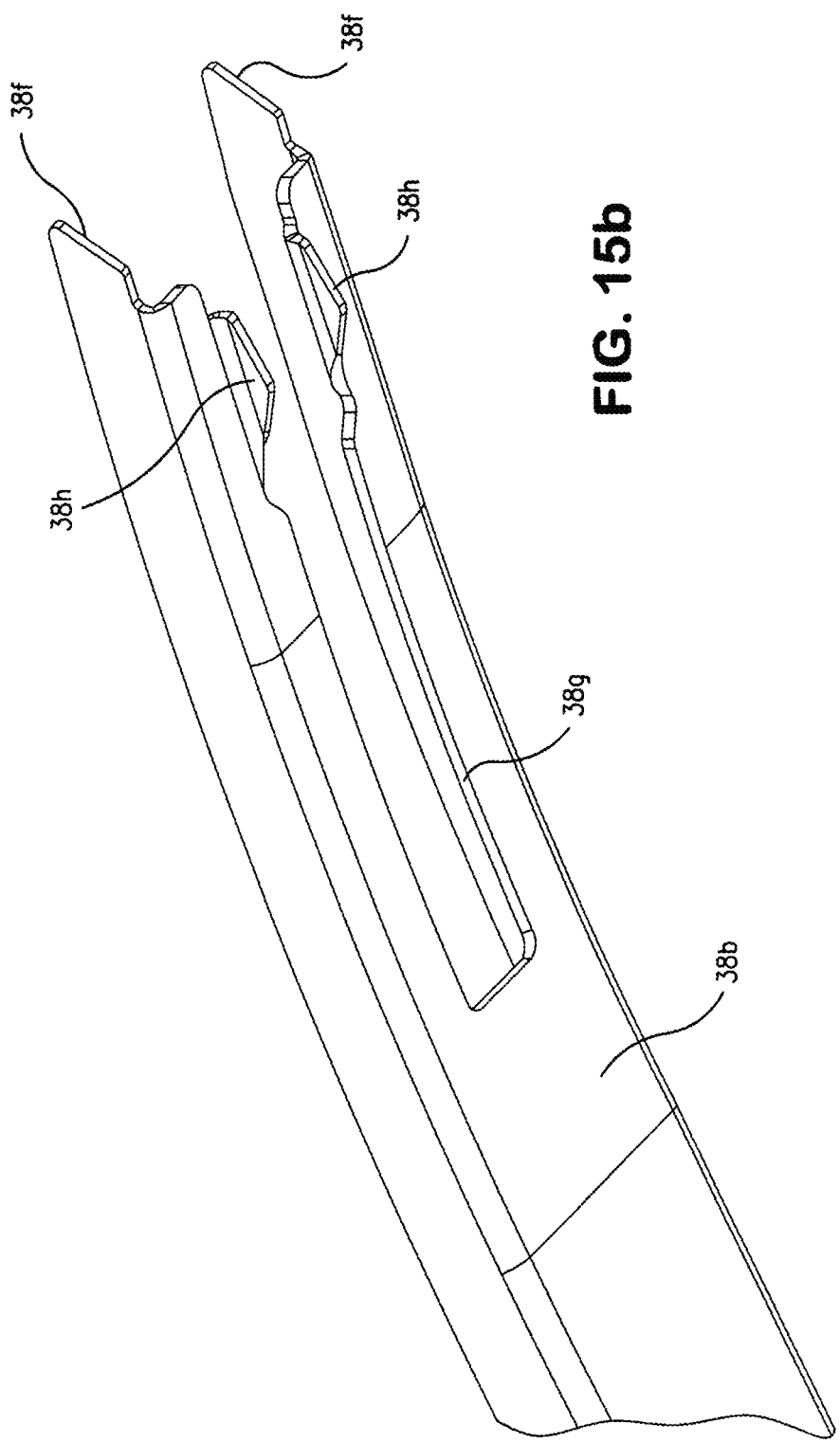

Referring to FIG. 13 illustrating frame 24 from below, pawl is assembled to frame as pawl pin 30c passes through triangular plate 24e. Pawl centering post 30g registers with arcuate rack in frame and limits extent of pawl rotation on pawl pin. Pawl control spring 30b is coil mounted on pin 30c with a pair of tangentially extending spring fingers 30h the ends of which overlap each side of pawl post for centering pawl in arcuate track. Spring fingers are moved by pawl against spring force developed by the coil.

In FIG. 13, the clip applier is in open position with puller bar in distal position. Pawl edge 30f is centered in proximal notch 36g and post 30g is centered in track 24g. When handles operate, puller bar moves to proximal and pawl edge passes out of notch and engages ratchet teeth surface and drags over ratchet teeth allowing continued proximal motion and preventing distal motion of puller bar and handle arms. So, proximal motion of puller bar must continue until pawl edge arrives at distal notch permitting pawl to toggle over thereby allowing reverse motion of instrument components under force of puller bar return spring. These operating components are referred to as anti-backup mechanism having an instrument open position with pawl centered in proximal notch. As handle arms are squeezed, puller bar moves to proximal, pawl edge 30f rotates slightly to proximal as it leaves notch and drags along ratchet teeth. Coil spring fingers 30h acting on pawl post 30g urge pawl in direction counter to puller bar motion thereby keeping pawl edge in engagement with ratchet teeth. Pawl edge in dragging acts as a wedge preventing reverse (distal) movement of puller bar. When puller bar reaches end of linear reciprocal movement, pawl edge enters distal notch, toggles over centering the pawl, and reverse (distal) movement of puller bar occurs by force of return spring 52 as handles are released.

Figure 16B:
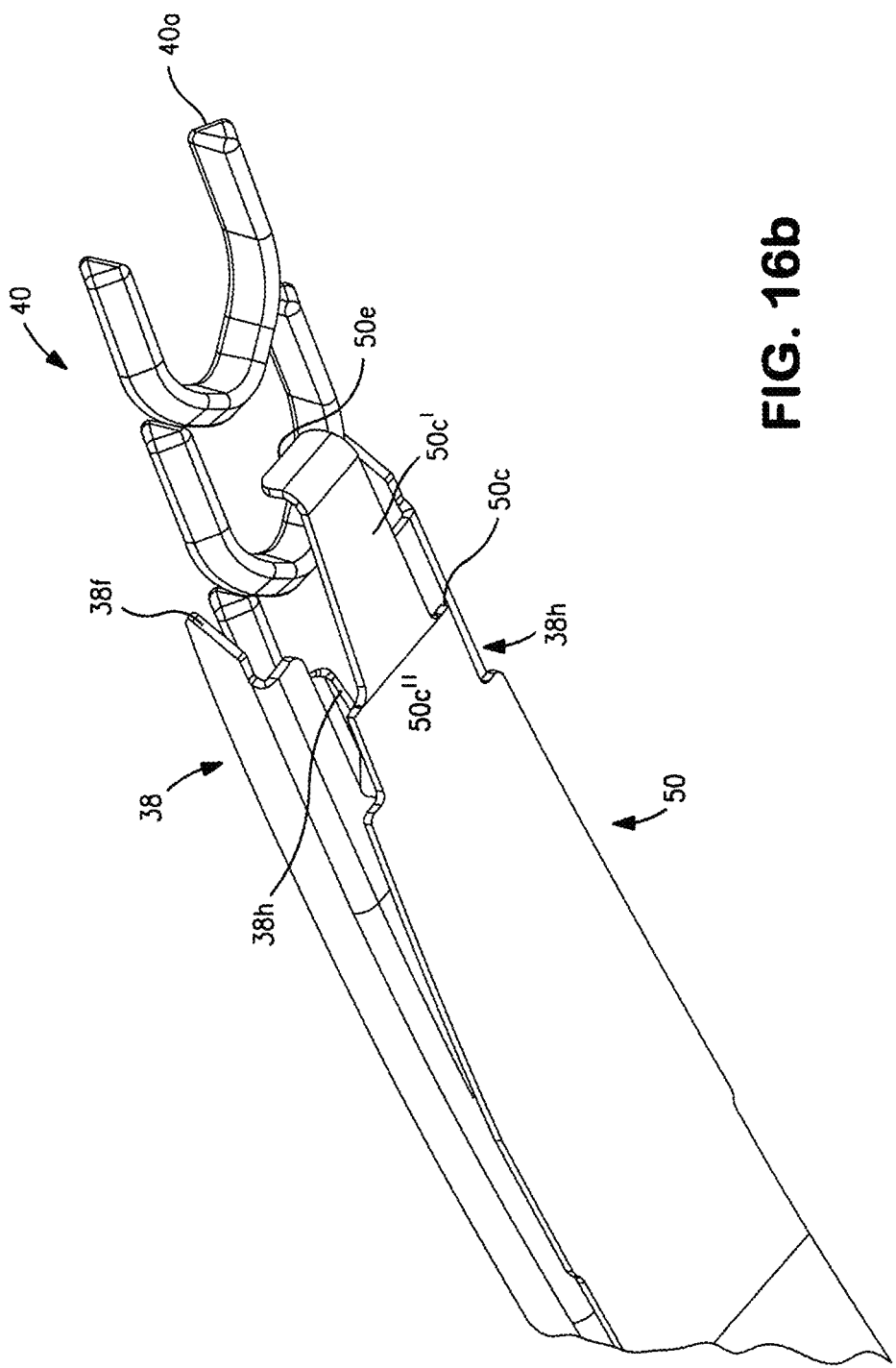
FIG. 16b is an underside view of clip retractor and magazine of FIG. 16a engaging a line of clips.

Clip retractor 50 (FIGS. 8 and 14) is an elongate strip metal stamping with proximal aperture 50a received by puller bar cam bar pin 36a, with an up-step 50b to pass up and over cover slot 16o (FIG. 7a) so as to locate retractor in cover channel 16n for cooperation with clip handling components. Retractor distal surface 50d curves downward to jaw point (when pressed against magazine FIG. 16b) terminating in upturned tip 50e. Distal surface further has side edge hips 50c for narrowing width of retractor adjacent tip 50e so as to enable the tip to move into and out of engagement with a stack of clips in the magazine as more particularly described below. The clip retractor is moved by the puller bar and pulls stack of clips proximally leaving foremost clip positioned in the jaws for individual closure around vessel in surgery.

The interior components thus described are assembled in the chassis, and the cover is set in place over components and handle and sealed to the chassis by suitable means 14a-b. In addition, cover opening 16p (FIG. 7a) press fits to chassis post 26.

Cover components have an assembly progression in which magazine 38 is assembled to the magazine carrier lens 46 and such assembly together with clip retractor 50 are snapped into cover slot 16n. This assembly of cover components is joined to previously assembled chassis comprising its operating components and handles. Clips are fed into closed magazine chamber defined by magazine 38 and lens 46 through cover port. Pusher 42 with mounted pusher spring 44 is compressed and inserted into open port to follow the clip stack 40. The pusher is then released to provide biasing force to the clips. Pusher spring cover 48 is snapped into place to complete device assembly.

Magazine 38 (FIGS. 3, 8, 15a-b, and 16a-b) carries a stack or line of clips 40, clip pusher 42, and clip pusher spring 44. The magazine and its carried components reside in the cover channel 16n immediately above clip retractor 50. Together the magazine and clip retractor regulate movement of clips serially into clip applying jaws. The clip stack, clip pusher, and clip pusher spring are assembled and placed within the magazine clip track. The clip pusher mounts the clip pusher spring and transfers force to the clip stack. Clip pusher post supports the spring which generates force for pushing the clip stack into the jaws.

Magazine 38 comprises elongate channel 38a of base 38b and side walls 38c-d accommodated fully within the magazine lens carrier 46. The channel defines a track for clips and carried components. Magazine distal end 38e curves downward to direct clips into jaws entry, and is configured for cooperation with clip retractor for serially feeding clips into the jaws. Side wall front edges 38f (FIGS. 15b and 17) are spaced across clip entry to jaws. Edges 38f are raked to conform to jaw profile at 32j and maintain maximum contact with clip prior to entry into jaws. As best seen in FIG. 17, raked edges 38f do not fall into the path of closing jaws.

U-shaped slot 38g in channel base opens through distal end of the channel. A pair of triangular flanges 38h are aligned across the slot, extend below channel base, and function as deflector tabs for regulating movement of clip retractor in controlling flow of clips into the jaws. The distance between deflector tabs 38*h* is greater than width of retractor on distal side 50*c*' of hips 50*c*, and less than width of retractor on proximal side 50*c*" of hips with the results that when retractor moves distally retractor tip is deflected by tabs away from clip stack. When moving proximally hips 50*c* move past tabs 38*h* so that tip 50*e* springs back toward clip stack. The clip retractor as it moves distally disengages clip stack as retractor hips encounter deflector tabs (FIGS. 16*a*-*b*) positioned under the magazine. Clip stack is thus released so line of clips pushes next clip into the jaws. Retractor movement away from jaw point moves hips 50*c* clear of magazine deflector tabs and releases the retractor tip to reengage clip stack.

FIG. 17 shows magazine 38 with clip stack 40 pushed into jaws that are carried by frame 24. The magazine with clip stack is positioned by cover 16 (FIG. 7*a*), while jaws and frame are positioned by chassis 18 (FIG. 6*a*). Jaw heads 32*c* are offset from jaw arms 32*b* to provide for clip entry 32*e* from magazine. Retractor tip 50*e* is in forward-most distal position and is deflected away from line of clips. On squeeze of handles, retractor 50 is pulled by puller bar cam pin, slips past magazine deflector tabs 38*h* to engage and pull clip stack to proximal leaving a first clip 40*a* in the jaws. Jaw closure for crimping and applying the clip in surgery is delayed as puller bar cam pin moves through slot 34*d* (FIG. 9) before engaging and pulling the cam bar for closing the jaws.

Figure 7A:
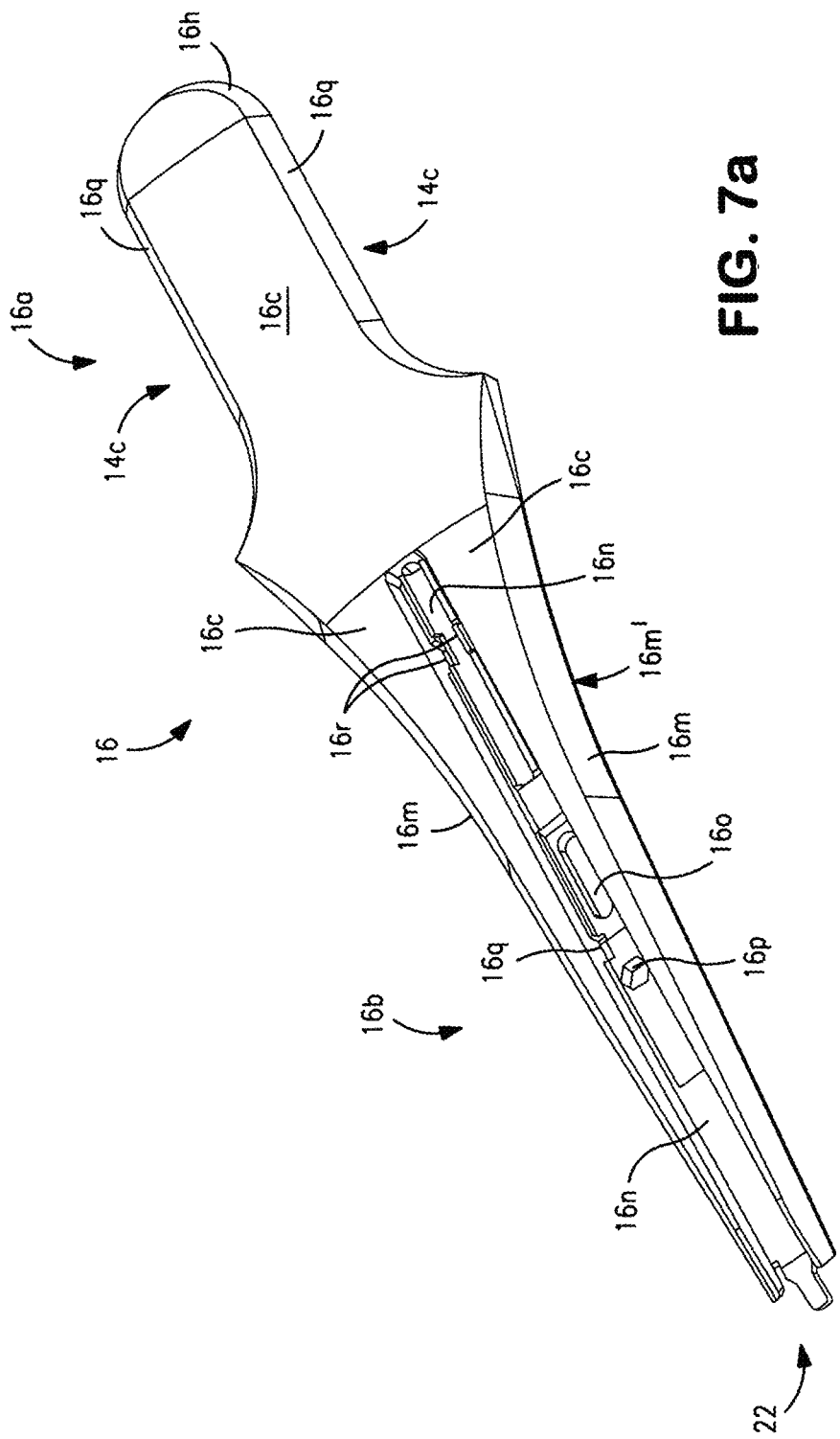
FIG. 7a is a topside perspective view of the exterior configuration of the cover of the instrument of FIG. 1.
Figure 7B:
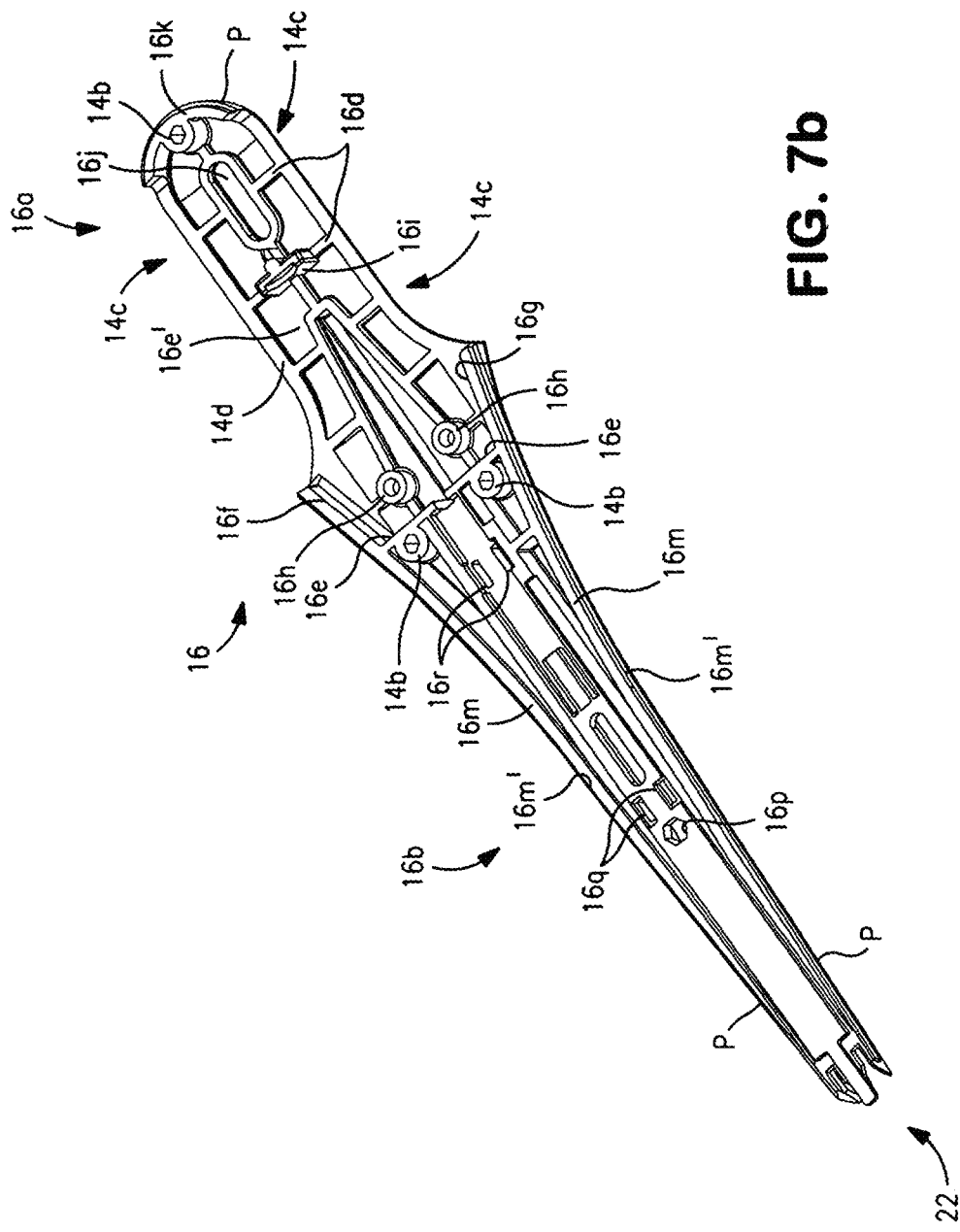
Figure 9:
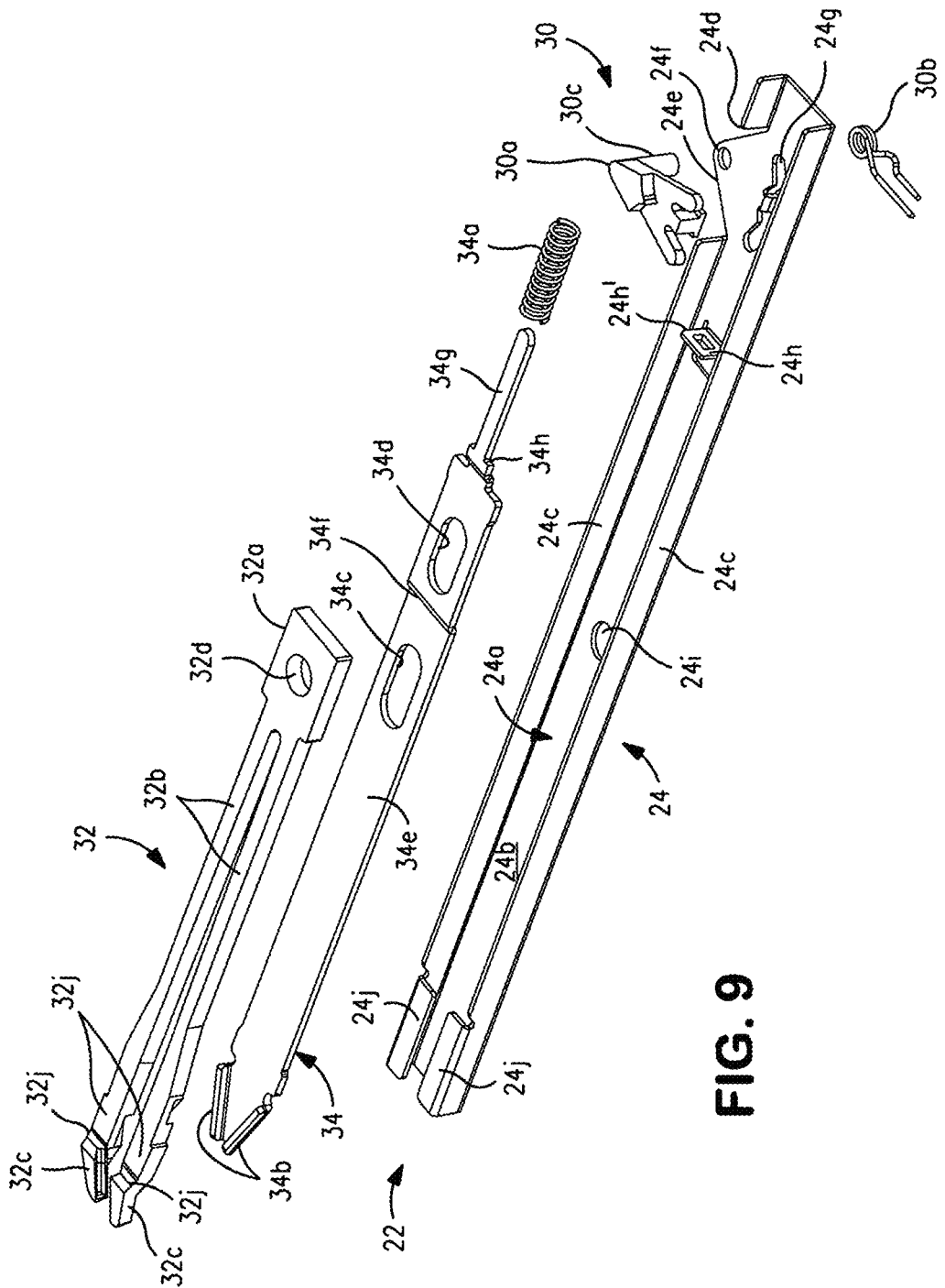
FIG. 9 is an exploded top perspective view of jaw operating parts shown in FIG. 8.
Figure 10:
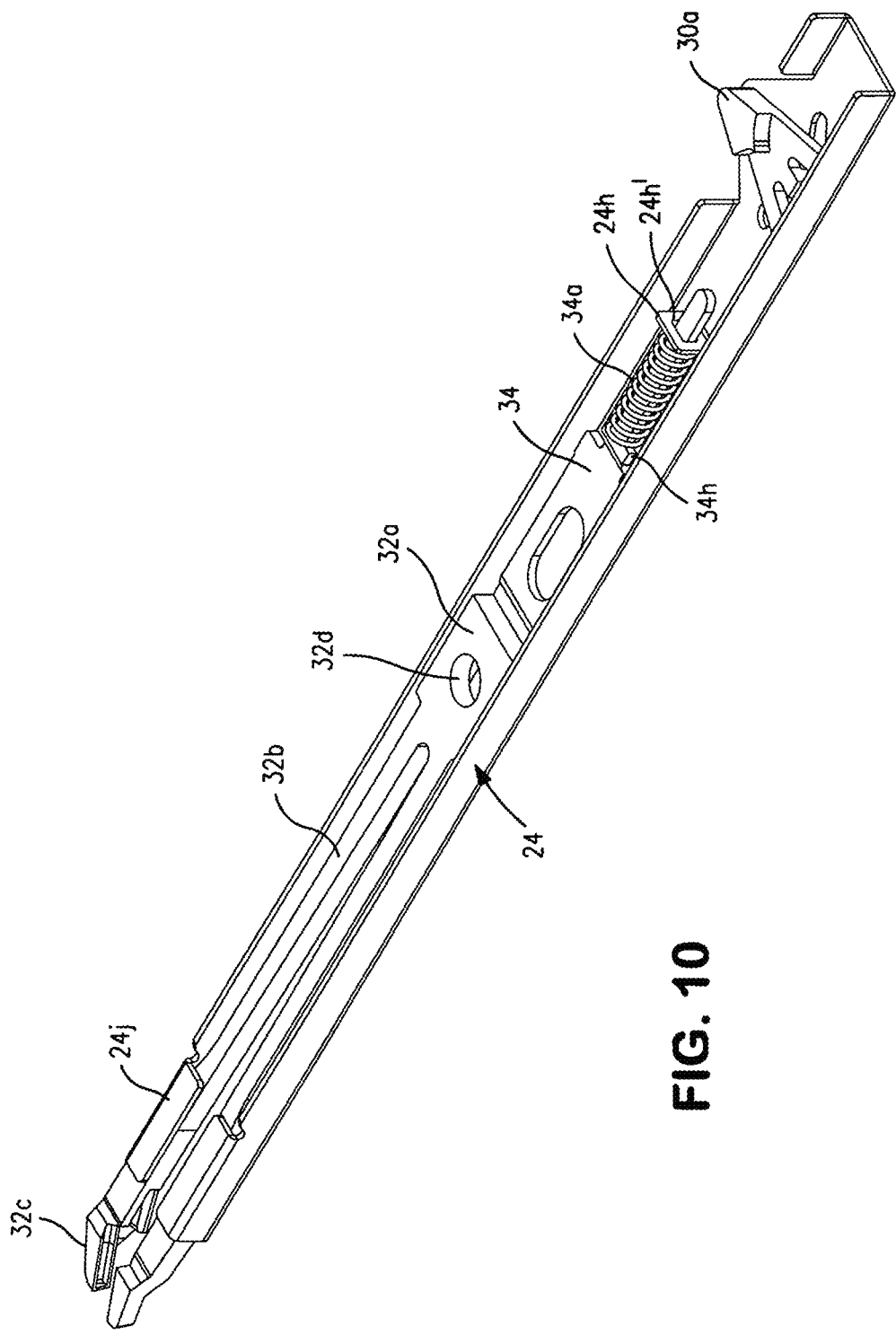
FIG. 10 is a top perspective view of an assembly of jaw operating parts illustrated in FIG. 9.
Figure 11A:
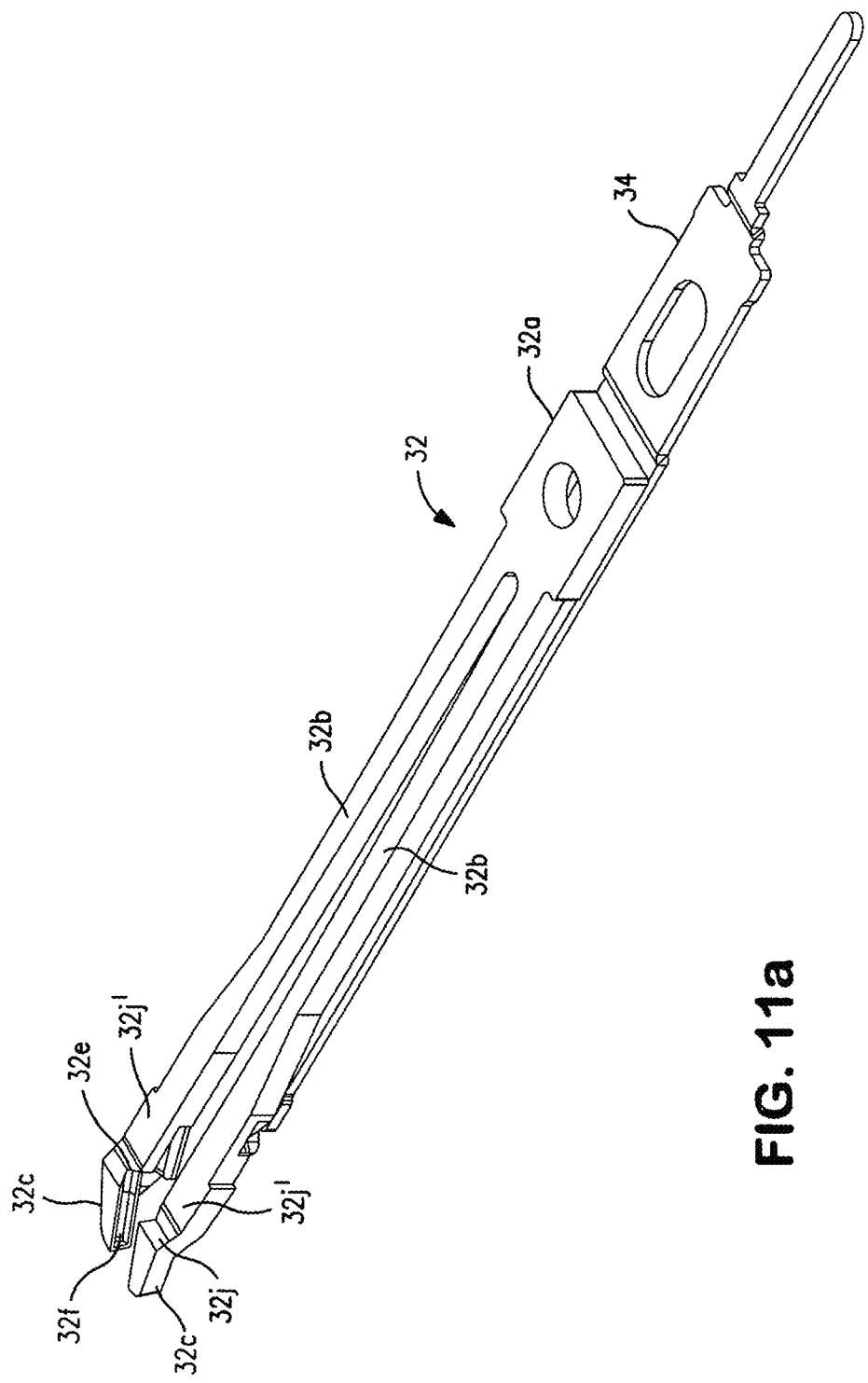
FIG. 11a is a top perspective view of a subassembly of jaws and jaws actuating cam bar illustrated in FIG. 10.
Figure 11B:
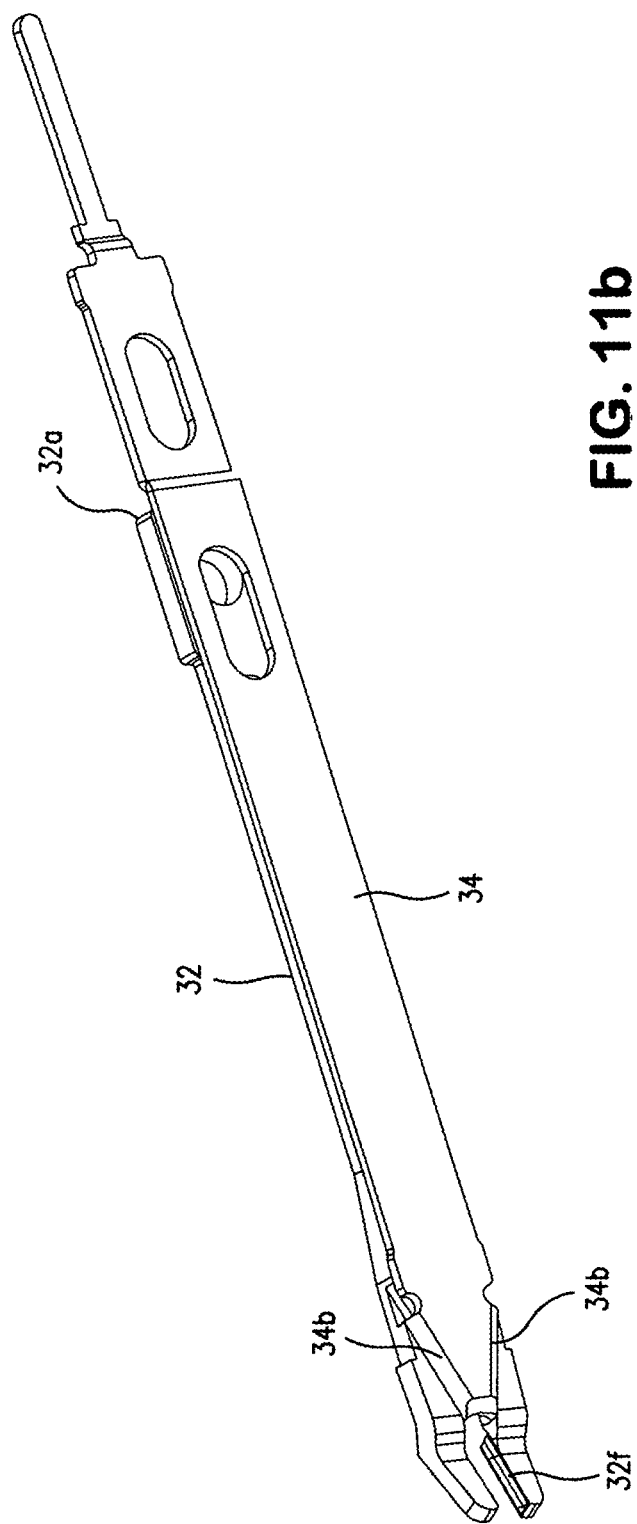
Figure 11C:
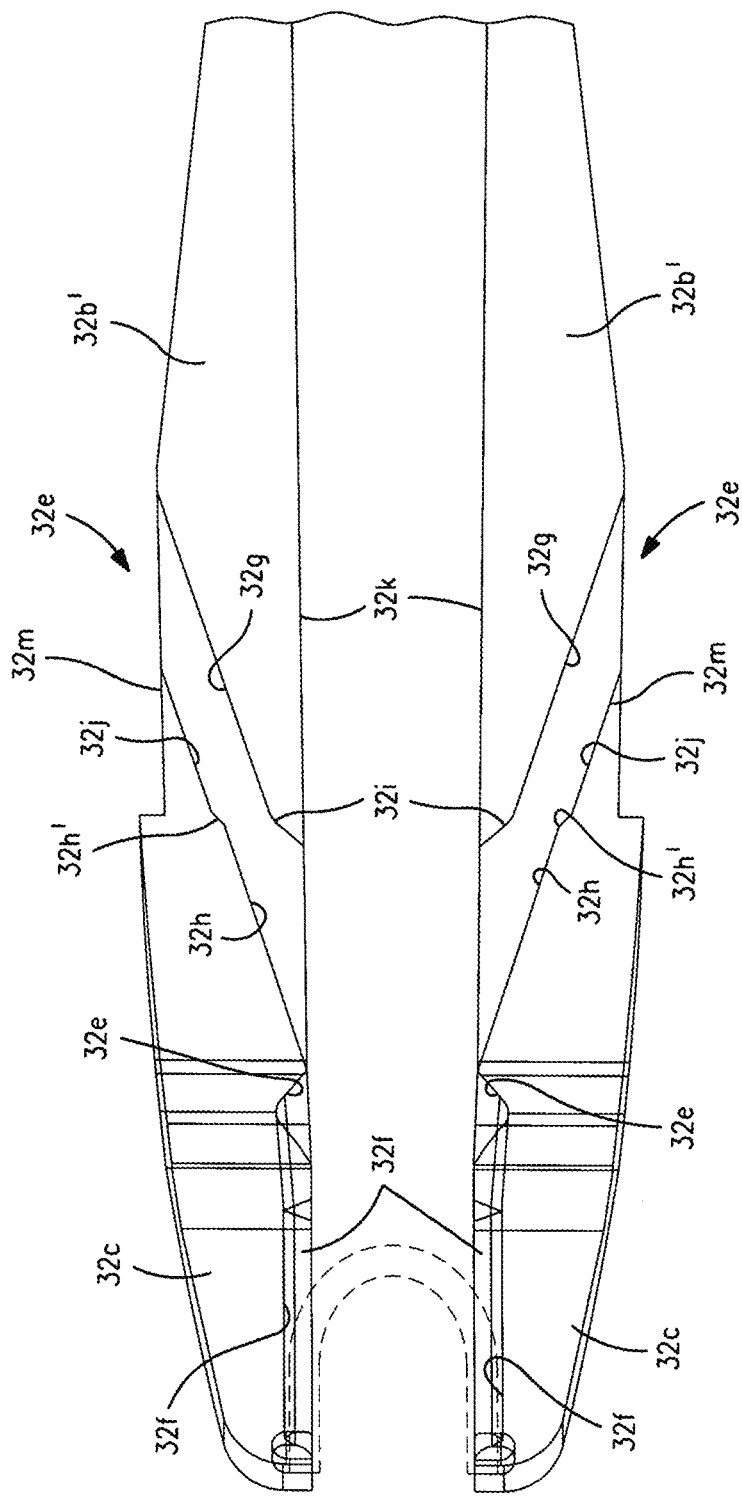
FIG. 11c is a bottom plan view of jaws of FIG. 11a showing cam grooves.
Figure 11D:
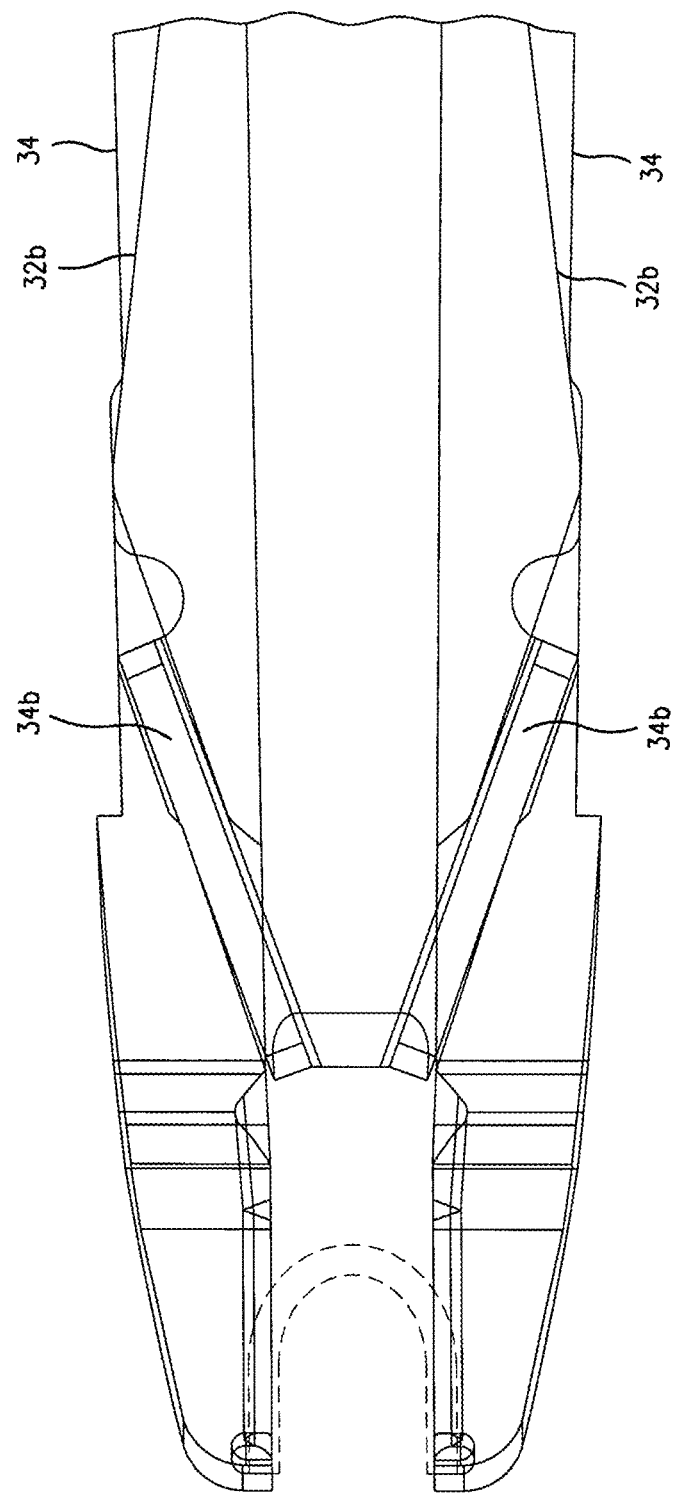
Figure 18A:
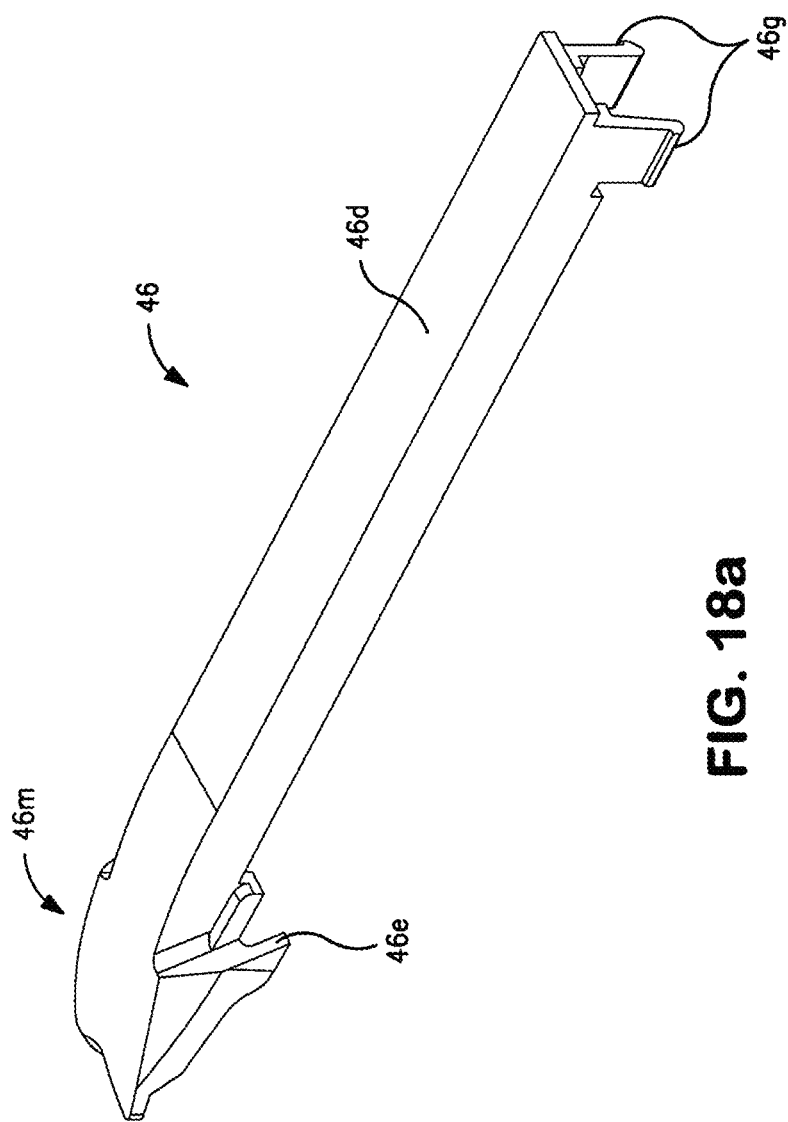
FIG. 18a is a top perspective view of the magazine carrier lens of the instrument of FIG. 1.

Magazine carrier lens 46 (FIGS. 18*a*-*c*) comprises a transparent clip cover that mounts into the cover channel and together with magazine defines clip track 46*f* for clip stack, clip pusher 42 (FIG. 3), and clip pusher spring 44. Carrier lens is a transparent elongate channel 46*a* comprising side walls 46*b*-*c*, top wall 46*d*, and curved distal end 46*m* for directing clips to jaws entry. Carrier lens nests within cover channel and is held in place by distal flat tabs 46*h*. Raked side edges or tabs 46*e* of carrier lens lock distal end of cover 16 to chassis 18 (FIG. 20) and with proximal flanges 46*g* snapped into and retained in cover slots 16*q* (FIG. 7*a*). Interior flat tabs 46*h* along side walls between distal side edges 46*e* rest on top of in-turned frame flanges 24*j* (FIG. 9). Carrier lens side wall end faces 46*i* (FIG. 20) abut jaw steps 32*j* for precise positioning of carrier lens and its clip track to jaw entry. The carrier lens nose 46*j* is notched conforming to depth of clip (FIG. 19) so as to allow viewing of entire clip situated in the jaws, and to allow vein to completely enter clip for ligation, and not to push further. Carrier lens distal side edges 46*e* abut chassis raked front edges 18*s*.

Figure 18B:
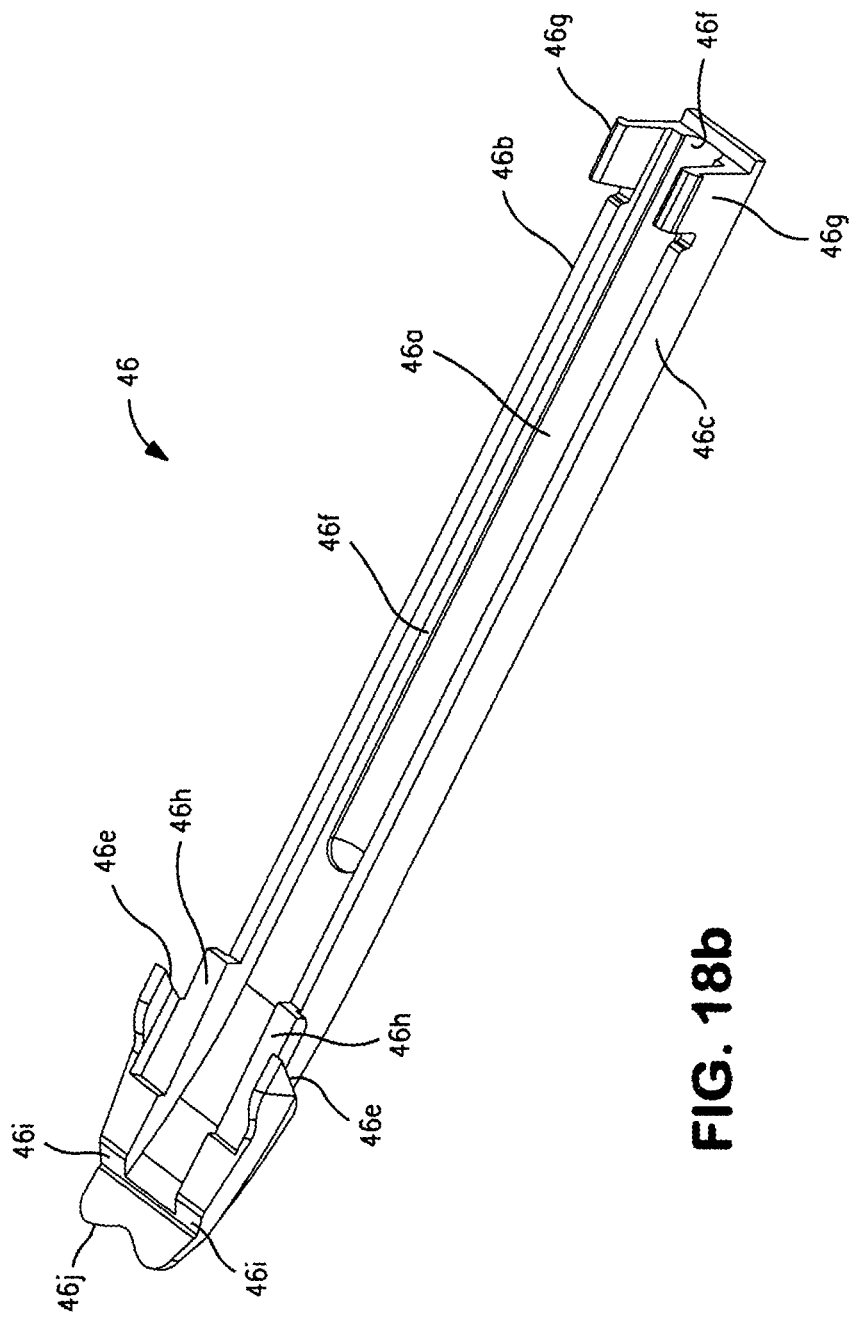
Figure 18C:
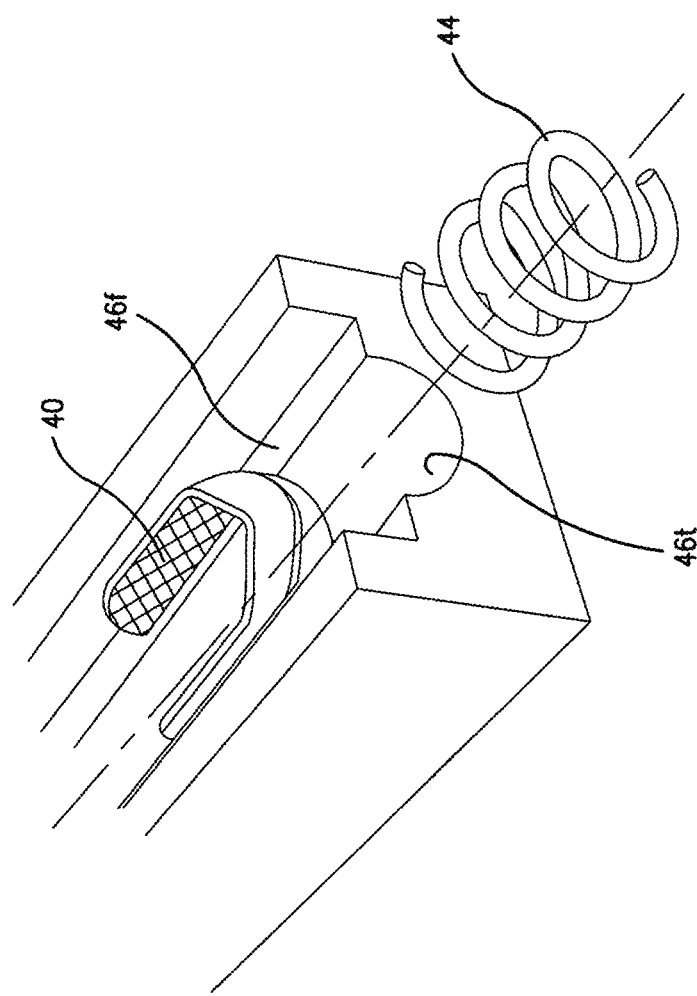
FIG. 18c is an inside fragmentary perspective view of the carrier lens of FIG. 18b showing positions of clip and pusher spring.

The carrier lens mounts on the cover and provides clip inventory visualization during surgery. The clips are inserted into the carrier from rear after full instrument assembly. The clip pusher and clip pusher spring are assembled and together they are inserted through the rear of the magazine carrier after full instrument assembly. FIGS. 18*b*-*c* show carrier lens interior with clips riding on flat surface clip track 46*f* and being pushed along by clip pusher 42. Cylindrical trough 46*t* provides clearance for axial travel of clip pusher and pusher spring 44.

Figure 21A:
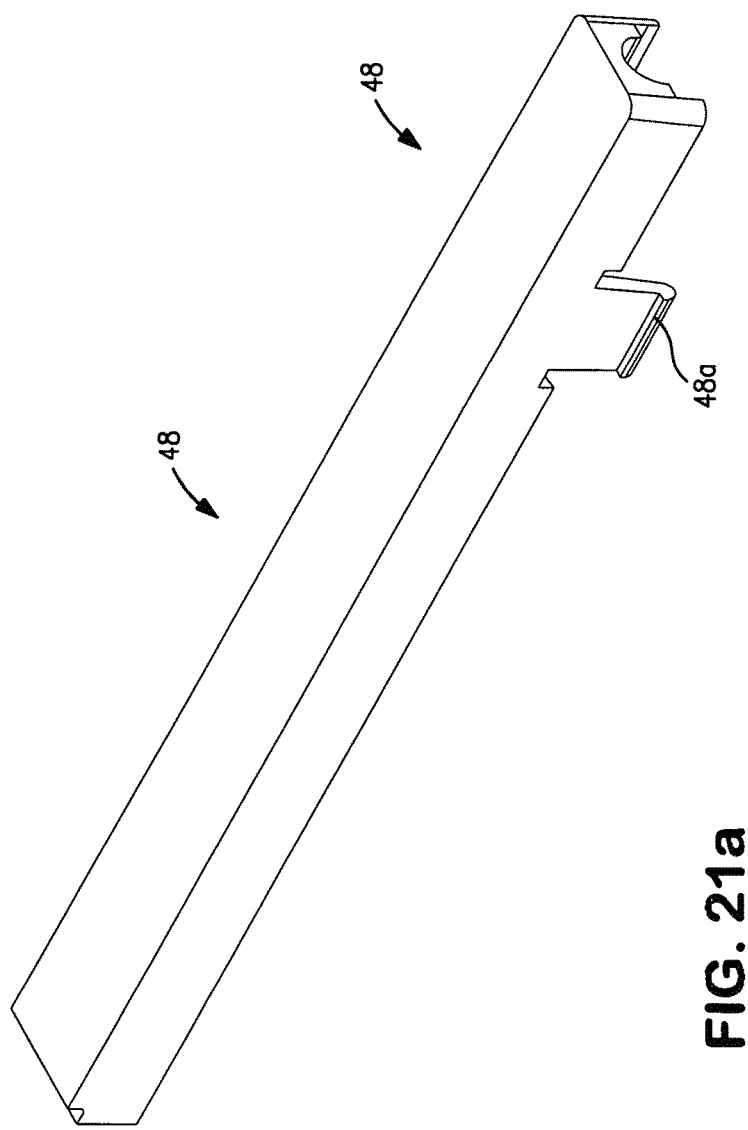
FIG. 21a is a top perspective view of the pusher spring cover of the instrument of FIG. 1.
Figure 21B:
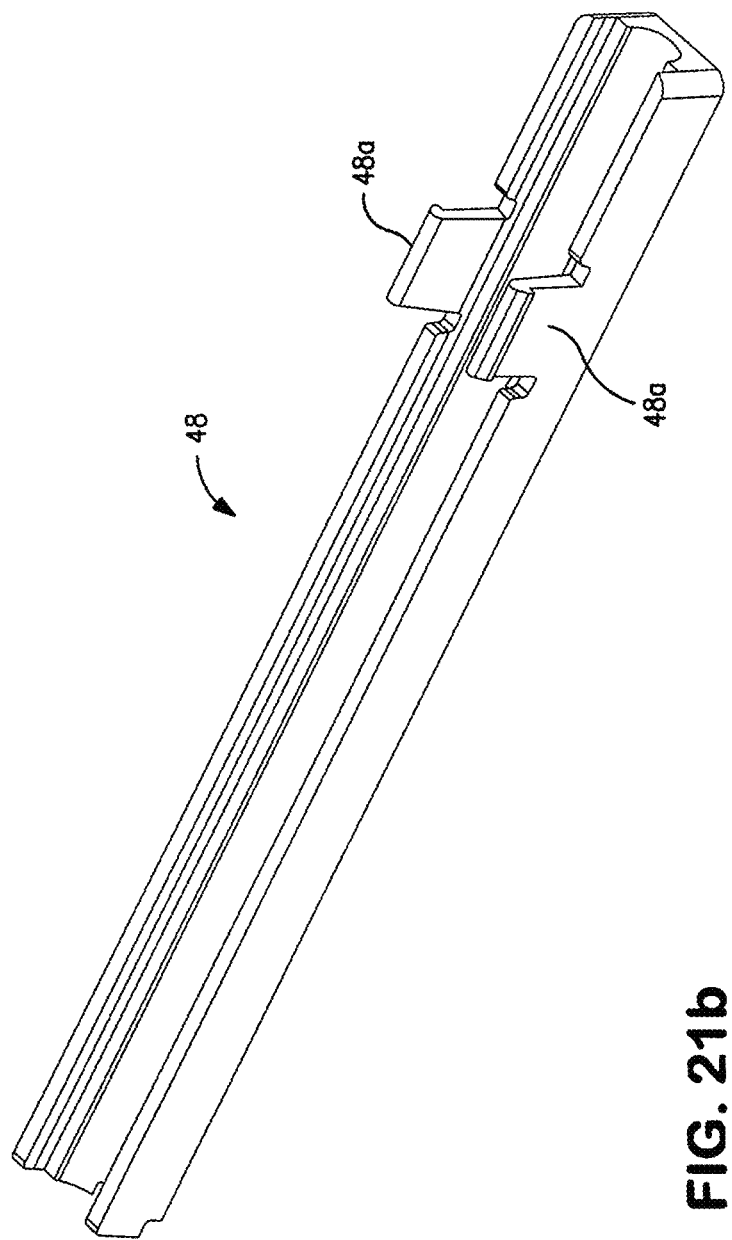

Finally, the pusher spring cover 48 (FIGS. 21*a*-*b*) is placed over the opening retaining these components and snapped into the cover with tabs 48*a*. The cover represents the last component in the instrument assembly.

In operation, with a pull and release of the handles, a clip is applied in surgery, and a clip is fed into the jaws.

Figure 22:
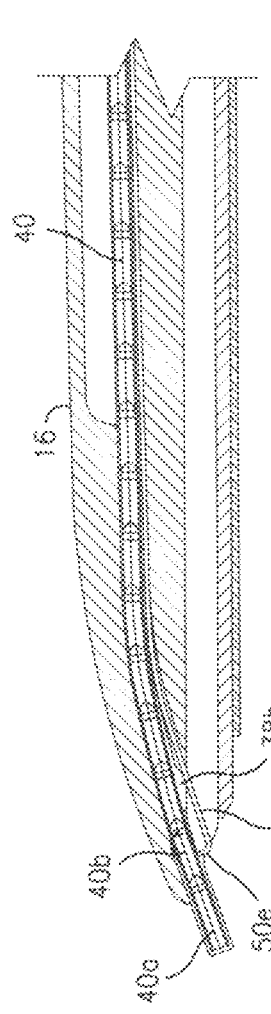
FIG. 22 is a section view of the distal end of the instrument of FIG. 1 with operating components at rest.
Figure 23A:
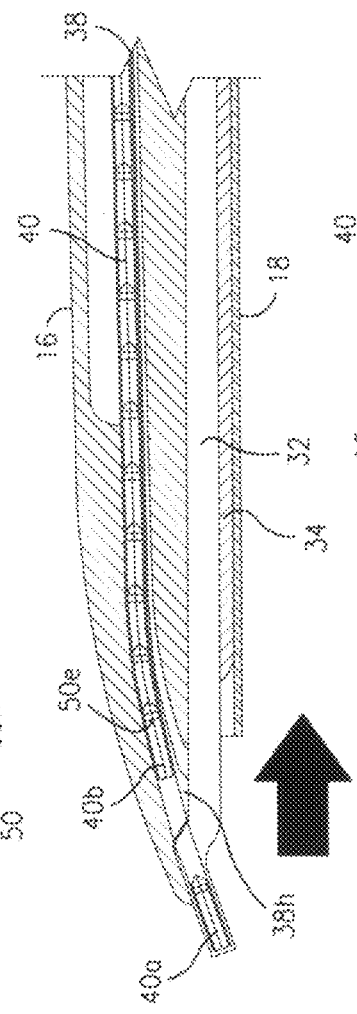
FIGS. 23a-b are section views of the distal end of the instrument of FIG. 1, which views taken together illustrate sequential movement of clips and their actuating components.
Figure 23B:
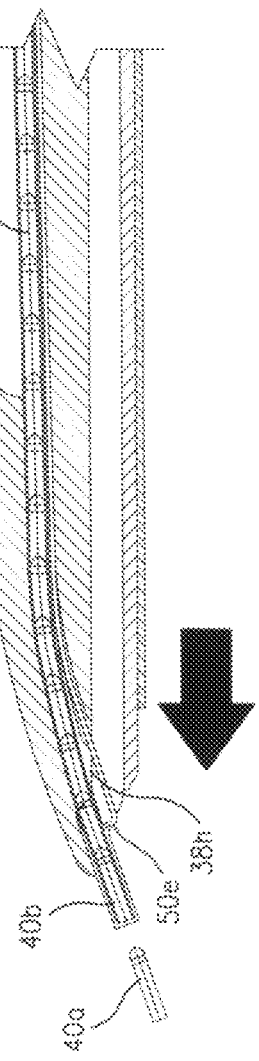

FIGS. 22 and 23*a*-*b* show clip movement sequence through clip applier operation. FIG. 22 shows clip applier at rest with handles open, and clip line 40 pushed into jaws, and with clip retractor bar 50 deflected by magazine tabs 38*h* to be out of engagement with clip stack. Clip track 40 exists between cover and magazine base where full clip stack is pushed to distal by pusher spring and in FIG. 22 is shown in forward position with clip retractor tip 50*e* disengaged from stack and with clip 40*a* in jaws. Clip 40*b* in FIGS. 22 and 23*a* is engaged and retracted by tip 50*e*, and after release in FIG. 23*b*, clip 40*b* is pushed into the jaws.

A squeeze of the handles moves puller bar to proximal:
  (i) clip retractor moves to proximal past deflector tabs so retractor tip engages first in line clip behind jaws and retracts clip stack to proximal;
  (ii) after delay, cam bar moves to proximal and closes jaws to apply clip in surgery;
  (iii) anti-backup mechanism pawl edge engages puller bar ratchet edge thereby constraining puller bar (and handle) movement to full pull stroke; and Release of the handles (FIG. 23*b*) allows return spring to move puller bar to distal:
  (i) clip retractor moves to distal with puller bar, reengages deflector tabs and disengages clip stack at end of distal stroke,
  (ii) and clip pusher spring moves stack to distal landing lead clip in jaws;
  (iii) when puller bar moves to distal, cam bar is free to move to distal with assistance of return spring, and so cam bar ramps working in cam grooves push jaws open;
  (iv) anti-backup mechanism pawl edge engages puller bar ratchet edge thereby constraining puller bar (and handle) movement to full release stroke.

Figure 8:
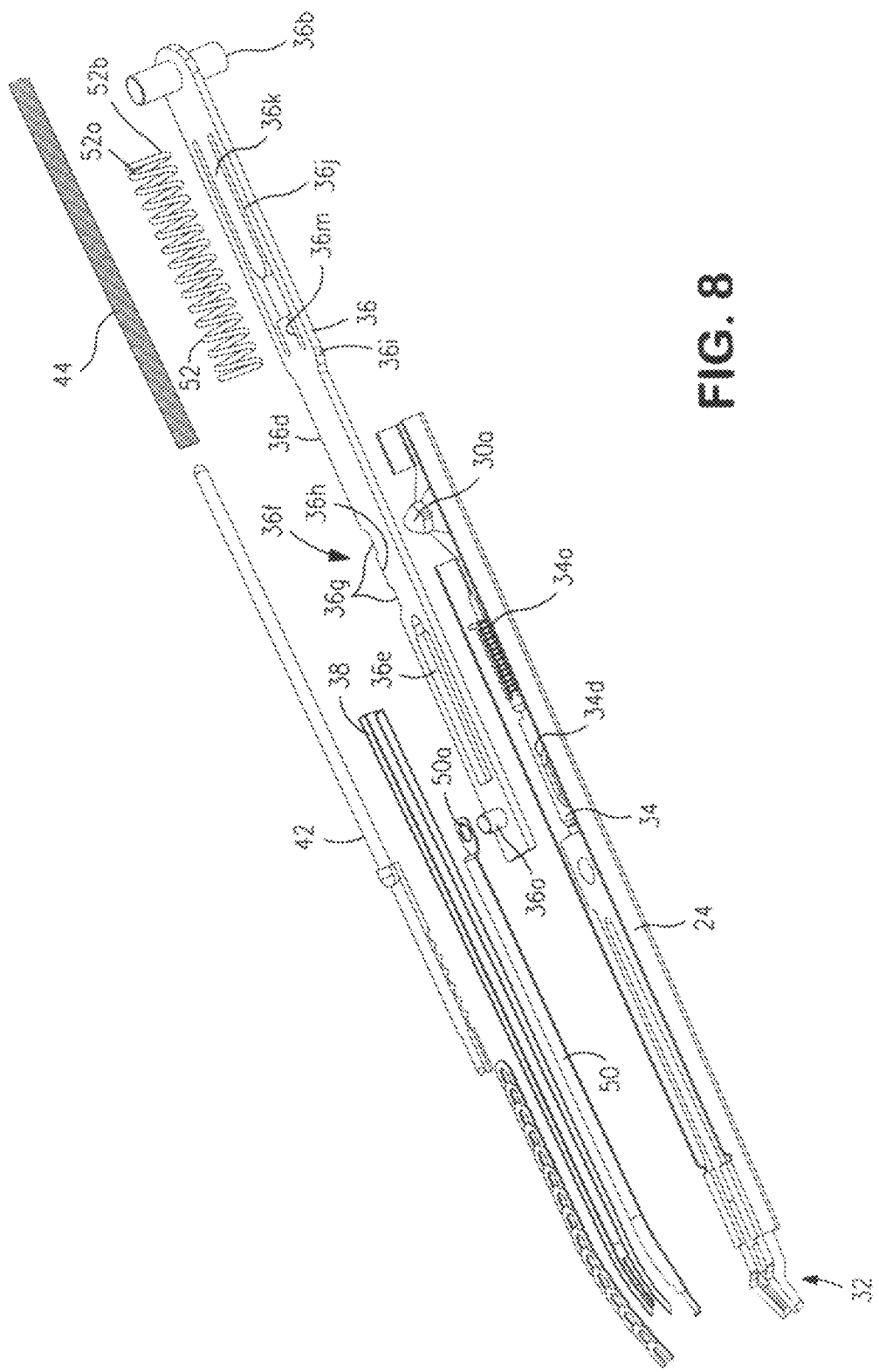
FIG. 8 is a top perspective view of full complement of instrument working component parts of the instrument of FIG. 1.

In FIGS. 3, 8, and 9 puller bar cam bar pin 36*a* and jaw post 26 are positioned at distal ends respectively of cam bar pin slot 34*d* and jaw post slot 34*c*. The pin slot is for delaying cam bar movement for closing jaws until clip retractor pulls clip stack back from the jaws clearing the jaws while leaving first clip in the jaws. After delay, cam bar closes jaws to apply clip in surgery.

Figure 24:
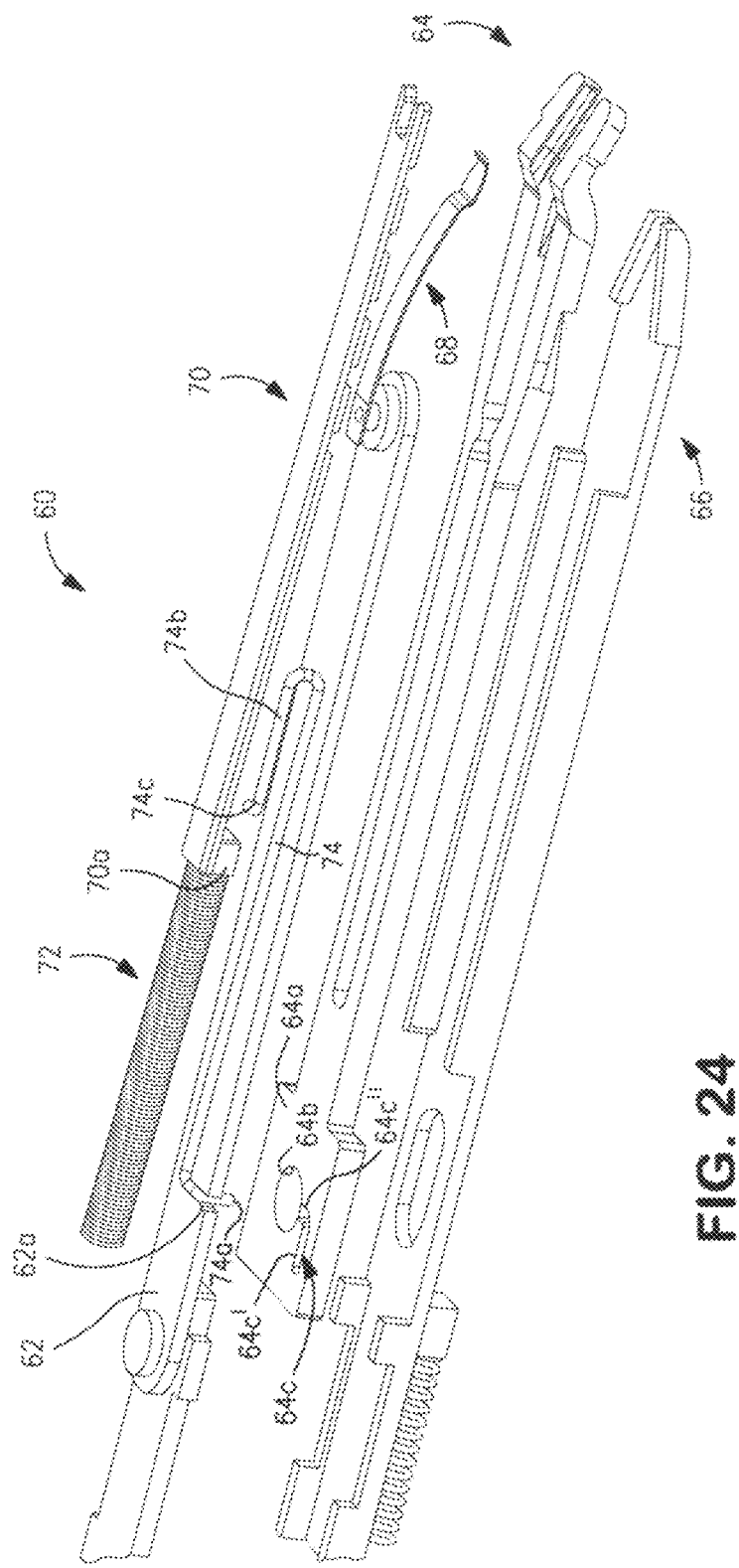
FIG. 24 is an exploded view of a modified embodiment of the invention showing a lockout mechanism to disable instrument after the last clip is used.

FIG. 24 illustrates a modified embodiment of the invention in providing a lock-out mechanism 60 after last clip is applied in surgery, so as to disable instrument against further use.

Instrument components shown include clip puller bar 62, jaws 64, jaws cam bar 66, clip retractor 68, clip pusher 70, and pusher spring 72.

Jaw base 64*a* includes jaw post mounting bore 64*b* and jaw lock slot 64*c* with linear run 64*c*' and transverse run 64*c*" communicating with bore. Puller bar 62 has side edge lock out slot 62*a* that aligns with transverse run 64*c*" of jaw lock slot when puller bar is at forward (distal) end of linear reciprocating movement.

Lock out spring 74 lies axially of puller bar with lockout spring tang 74*a* at one end for cooperation with jaw lock slot, and reverse run section 74*b* of spring with reverse run tang 74*c* for cooperation with clip pusher 70 and clip pusher shoulder 70*a*.

In initial instrument operation beginning with a full stack of clips, lock out spring overlies puller bar with lockout tang reposing in linear run of jaw lock slot, and with reverse run tang nestled under clip pusher well forward of pusher shoulder. Being mounted on puller bar, the lock out spring will have same range of linear reciprocation movement but nevertheless with lockout tang remaining in linear run and reverse run tang well clear of pusher shoulder at all times. As last clip is used in surgery, the following lockout sequence occurs:

(i) tip of clip pusher enters and remains in jaws;

(ii) pusher shoulder engages and moves reverse run tang a clip length to distal while at the same time moving lockout spring tang to clear linear run, move through transverse run and enter puller bar lockout slot;

(iii) locking puller bar to stationary jaws to prevent any linear reciprocating movement;

(iv) with clip pusher spring continuing to hold pusher tip in the jaws with the result that (v) no further instrument operation is possible.

The term approximately for purposes of this application means plus or minus 10% of the values stated.

Various changes may be made to the structure embodying the principles of the invention. The foregoing embodiments are set forth in an illustrative and not in a limiting sense. The scope of the invention is defined by the claims appended hereto.

I claim:

1. An instrument for applying clips in surgery comprising:

a housing defined by a chassis and a cover, the chassis of unitary construction having a handle section, an instrument components section, side walls, an open front end, and a rear wall, the cover of unitary construction having a handle section, a clip handling components section, side walls, an open front end, and a rear wall, the chassis and the cover joined at their side walls and rear walls to form the housing;

a pair of handle arms, the housing having handle gaps in between the side walls and the rear wall of both the chassis and the cover to provide access to an interior chamber for accommodating the handle arms, the chassis and the cover secured to each other by fasteners, the open front ends of the chassis and the cover defining a jaw point;

a first set of instrument components, the chassis having an interior channel extending toward the jaw point between the side walls of the chassis, wherein the first set of instrument components are positioned within the interior channel of the chassis;

a jaw post affixed to the interior channel;

a second set of instrument components, the cover having a top wall and an exterior channel in the top wall of the cover extending toward the jaw point, wherein the second set of instrument components are positioned within the exterior channel, the first set of instrument components positioned in the chassis interior channel includes a cam bar positioned on the jaw post;

a pair of jaws mounted on the jaw post for applying clips in surgery, the cam bar actuatable for closing the jaws;

a puller bar cooperating with the cam bar and the handle arms for imparting motion to the first set of components, and the puller bar having a return spring for urging the handle arms to an open position, the second set of instrument components positioned in the cover exterior channel including a magazine, a line of clips in the magazine, a pusher to advance the line of clips to advance a clip into the jaws, and a pusher spring, a clip retractor connected to the puller bar for moving the line of clips proximally, wherein after a last clip of the line of clips is used, a tip of the pusher enters and remains in the jaws and the puller bar is locked to the jaws to prevent any puller bar motion.

2. An instrument as defined in claim 1 in which the housing has a longitudinal axis, and in which the channel and the cover are aligned along the axis.

3. An instrument as defined in claim 1 in which the handle arms pass through the handle gaps into the interior chamber, each handle arm pivotally connected to the chassis and the cover of the housing, and a linkage of link bars pivotally joined to the handle arms, whereby the handle arms generate linear reciprocating motion of fixed excursion.

4. An instrument as defined in claim 1 in which the pusher spring holds the tip of the pusher in the jaws, the puller bar having a puller bar lockout slot, the jaws having a base with a jaw lock slot, the jaw lock slot having a linear run and a tranverse run, a lockout spring overlying the puller bar, the lockout spring having a lockout tang and further having a reverse run section with a reverse run tang, whereby as the pusher tip enters the jaws, the pusher engages the reverse run tang to move the lockout spring distally so that the lockout tang moves along the linear run and by spring bias enters the transverse run of the jaw lock slot and there engages the puller bar lockout slot.

5. An instrument as defined in claim 1 which further comprises a frame positioned in the interior channel of the chassis, the frame comprising an elongate channel having a base plate with a stop shoulder on the base plate of the frame, the frame receiving the first set of instrument components including the jaws, the cam bar, and the puller bar, the frame having an aperture for accommodating the jaw post, and the cam bar having the return spring held in place by the stop shoulder.

6. An instrument as defined in claim 5 further comprising an anti-backup mechanism of a pawl, a pawl spring, and ratchet teeth on the puller bar, the frame having an extension of its base plate with an aperture for mounting the pawl for cooperating with the puller bar ratchet teeth to limit the puller bar motion and the handle arms motion to full pull and release strokes.

7. An instrument as defined in claim 3 in which the handle arms and the linkage of link bars are connected by a single pivot pin and in which the puller bar is connected to the single pivot pin.

8. An instrument as defined in claim 1 in which the second set of components comprises a carrier lens and a pusher spring cover for enclosing the channel of the cover.

9. An instrument as defined in claim 8 in which the clip retractor passes through the channel of the cover for connection to the puller bar, the clip retractor moving proximally by the puller bar when the handles are compressed.

10. An instrument as defined in claim 1, wherein the chassis has a longitudinal axis, wherein the instrument further comprises a linkage between the handle arms, the puller bar having a pin connected to the linkage, each of the pair of handle arms having an arcuate lever body with an inner side, the inner side of each arcuate lever body extending along a length of the respective lever body, wherein an integral pier extends laterally inwardly and forwardly from the middle of the inner side of each lever body to provide a region of increased width, wherein each pier comprises a block with planar upper and lower surfaces enabling the respective pier to slide in and out of the handle gaps into the interior chamber, each pier having a longitudinal recess in a side wall between the upper and lower surfaces facing inwardly toward the longitudinal axis of the chassis to accommodate the linkage between the handle arms, each pier further having a puller bar recess to support the puller bar, the puller bar movable proximally to close the first jaw and the second jaw, each pier having a forward surface, wherein a pivot recess is situated at the forward surface of each pier, and wherein the chassis and the cover each have aligned pivot pins within the interior chamber for cooperation with the pier pivot recesses for pivoting the handle arms on the housing.

11. An instrument as defined in claim 10 in which each of the piers has first and second lateral recesses, the first and second lateral recesses extending into a side wall of each of the piers and extending inwardly away from a longitudinal axis of the chassis, the first lateral recess providing clearance for spring stops of the cover and chassis and the second lateral recess providing space for the pin of the puller bar.

12. An instrument as defined in claim 10 in which the arcuate lever body comprises a loopless ergonomic configuration for a gripping surface along an outer side of the lever body, the gripping surface having a ridge line convex in conforming to an inside surface of a thumb adjoining a palm.

13. An instrument as defined in claim 12 in which the gripping surface further has opposite side perimeter lines and a front perimeter line, the gripping surface further being of variable convexity from opposite side perimeter lines across the ridge line, with the ridge line changing from convex to concave as it nears the front perimeter line.

14. An instrument for applying clips in surgery comprising:
 a housing defined by a chassis and a cover, the chassis and the cover each being of integral construction and each incorporating a handle section and an instrument component section, the chassis and the cover secured to each other by fasteners, the chassis and the cover defining a jaw point where clips are applied;
 a first set of instrument components, the instrument component section of the chassis having an elongated interior channel in which the first set of instrument components are positioned;
 a pair of handle links and handle arms, the chassis handle section located at a proximal region and receiving the pair of handle links and handle arms;
 a jaw post affixed to said interior channel, the first set of instrument components comprising a frame situated in said interior channel over the jaw post, the frame having a distal end adjacent a distal end of the instrument component section of the chassis and having a proximal end positioned in the instrument component section of the chassis, the frame extending along a length of said interior channel and having side walls defining a frame channel;
 a cam bar in the frame channel, the cam bar having a first oval aperture positioned within the frame channel over the jaw post and having a second oval aperture;
 a pair of jaws, the jaws mounted on the jaw post, the cam bar further having ramps extending into the jaws for actuating the jaws, the jaws having an aperture at a proximal end mounted to the jaw post over the cam bar, the jaws terminating at a distal end adjacent the distal end of the instrument section of the chassis, the jaws having angled grooves in engagement with the ramps of the cam bar; and
 a puller bar over the cam bar, the puller bar having a pin cooperating with the second oval aperture for moving the cam bar and actuating the jaws, the puller bar having a proximal end and a distal end positioned within the chassis, the puller bar movable in a proximal direction to move the ramps of the cam bar proximally within the angled grooves formed by an inner and outer wall of the laws to close the jaws, the cam bar having a return spring for moving the cam bar distally, the cam bar terminating at its distal end adjacent the distal end of the instrument section of the chassis.

15. An instrument as defined in claim 14 in which the cam bar has an elongate tang, the return spring mounted on the tang, the frame having a spring stop with an aperture against which the return spring is compressed as the cam bar moves proximally to close the jaws, and the tang passing through the spring stop aperture in the frame to position the spring between the cam bar and the return spring stop.

16. An instrument as defined in claim 14 further comprising an anti-backup mechanism, the frame having a frame extension having an aperture, a pawl mounted in the aperture of the frame extension, a spring for centering the pawl on the frame, the puller bar having a side edge and a ratchet surface formed in a length of the side edge, a toggle groove in the side edge at each end of the ratchet surface, a pawl edge for engaging the side edge of the puller bar including the ratchet surface and the toggle grooves so that when the puller bar moves during instrument operation the pawl edge engages the ratchet surface constraining the puller bar to move in one direction until the pawl edge leaves the ratchet surface and enters the toggle groove enabling the pawl to toggle over and permit the puller bar movement in an opposite direction.

17. An instrument as defined in claim 14 further comprising an anti-backup mechanism, the frame having a frame extension with an aperture and a rack, a pawl having a pin situated in the aperture of the frame extension defining an axis of rotation for the pawl, the pawl having a post positioned in the rack, a spring coiled about the pin and having spring arms engaging the post for centering the pawl on the frame, the puller bar having a side edge and a ratchet surface formed in a length of the side edge, a toggle groove in the side edge at each end of the ratchet surface, the pawl having an edge for engaging the side edge of the puller bar including the ratchet surface and grooves so that when the puller bar moves during instrument operation the pawl edge engages the ratchet surface constraining the puller bar to move in one direction until the pawl edge leaves the ratchet surface and enters the grooves enabling the pawl to toggle over and permit puller bar movement in an opposite direction, and the spring arms urging the pawl in a direction opposite to the puller bar movement.

18. An instrument for applying clips in surgery comprising:
 a housing defined by a chassis and a cover, the chassis and the cover secured to each other by fasteners, the chassis and the cover defining a jaw point;
 a first set of instrument components, the chassis having an interior chassis channel, wherein the first set of instrument components are positioned within the interior chassis channel;
 a jaw post affixed to the chassis channel, the first set of instrument components comprising a cam bar in the chassis channel;
 a pair of jaws, the cam bar having an aperture over the jaw post and further having ramps for actuating the jaws, the jaws having jaw arms and a base mounted to the jaw post to lie over the cam bar, each of the jaw arms having cam grooves in engagement with the ramps of the cam bar, the cam grooves extending interiorly into the jaw arms, the cam grooves defined by spaced proximal and distal cam walls, the ramps of the cam bar move within the cam grooves formed between the proximal and distal cam walls, both the proximal and distal cam walls extending diagonally across the jaw arms and converging toward a head of each jaw and toward a central longitudinal axis of the instrument, each proximal cam wall turning toward an arm inner surface to define a crowned point for engaging each ramp of the cam bar to concentrate forces from each ramp at a fixed location such that the mechanical advantage between each cam wall and each ramp does not negatively shift as the cam bar moves proximally to close the jaws, the distal cam walls having relief notches to prevent a binding condition when the jaw arms flex to a closed position of the jaws.

19. An instrument for applying clips in surgery comprising:
- a housing defined by a chassis and a cover, the housing having handle arms, the chassis and the cover joined along edges and secured to each other by fasteners to form the housing, the chassis and the cover defining a jaw point where clips are applied;
- a first set of instrument components, the chassis having an interior chassis channel extending toward the jaw point between side walls, wherein the first set of instrument components are positioned within the interior chassis channel and include a cam bar, clip applying jaws, a puller bar within the housing, the puller bar connected to the cam bar for closing the jaws, and a jaw post affixed to the chassis channel for positioning the cam bar and the jaws;
- a second set of instrument components, the cover having a top wall, and an exterior cover channel in the top wall extending toward the jaw point, wherein the second set of instrument components are positioned within the exterior cover channel for cooperation with the first set of instrument components, the second set of instrument components comprising a magazine situated in the cover channel, a line of clips in the magazine, the magazine having a channel defining a clip track for the line of clips and curving downwardly at a distal end to direct the line of clips into the clip applying jaws, a pusher and a pusher spring for urging the line of clips toward the jaw point;
- a clip retractor connected to the puller bar and positioned in the cover channel beneath the magazine for selectively engaging and retracting the line of clips during instrument operation, wherein upon squeezing of the handle arms of the instrument, the clip retractor is pulled back to engage and pull the line of clips proximally to leave a distal clip of the line of clips in the jaws; and
- a carrier lens and a pusher spring cover enclosing the pusher and the pusher spring positioned in the cover channel.

20. An instrument as defined in claim 19 in which the carrier lens is assembled to the magazine to define the clip track for the line of clips, the pusher, and the pusher spring.

21. An instrument as defined in claim 19 in which the magazine and the carrier lens are assembled and together with the clip retractor are inserted into the cover channel.

22. An instrument as defined in claim 21 in which the magazine and the carrier lens when assembled define an open proximal end for receiving the line of clips, the pusher, the pusher spring, and the pusher spring cover for closing the open proximal end.

23. An instrument as defined in claim 19 in which the magazine has a channel base with a distal end U-shaped slot and a pair of deflectors on the magazine spaced across the slot, the clip retractor cooperating with the puller bar and the deflectors to retract the line of clips for isolating at the jaw point the distal clip in the line of clips, and for releasing the line of clips to advance to the jaw point.

24. An instrument as defined in claim 23 in which the clip retractor has an elongate strip connected at a proximal end to the puller bar, a distal upturned tip for engaging the line of clips, and a distal surface having hips along lateral surfaces of the strip, the distal surface on a distal side of the hips being narrower than a space between the deflectors, and the distal surface on a proximal side of the hips being greater than the space between the deflectors whereby the clip retractor retracts and releases the line of clips during instrument operation.

25. An instrument as defined in claim 19 in which the carrier lens is transparent for viewing the line of clips.

26. An instrument as defined in claim 19 in which, the jaws are stepped up to define an entry for the line of clips into the jaws, and further in which the magazine and the carrier lens have curved distal ends for directing the line of clips into the entry of the jaws.

27. An instrument as defined in claim 26 in which the carrier lens has a nose at the jaw point being notched to conform to a depth of the distal clip of the line of clips in the jaws, the notch allowing a vessel in surgery to completely enter the clip without pushing the clip.

28. An instrument as defined in claim 19 in which the side walls of the chassis are raked at the jaw point, and in which the carrier lens has distal side edges for abutting the side walls of the chassis.

29. An instrument as defined in claim 28 in which the cover is provided with slots, and the carrier lens has proximal flanges retained in the slots of the cover.

30. An instrument as defined in claim 22 in which the cover has a port for receiving a proximal end of the pusher as the pusher is assembled to the instrument.

* * * * *